(12) United States Patent
Goldsmith et al.

(10) Patent No.: US 9,504,678 B2
(45) Date of Patent: Nov. 29, 2016

(54) ORAL DOSAGE FORMS INCLUDING AN ANTIPLATELET AGENT AND AN ACID INHIBITOR

(75) Inventors: Mark A. Goldsmith, Menlo Park, CA (US); Elizabeth Vadas, Dorval, CA (US)

(73) Assignee: KG ACQUISITION LLC, New York, NY (US)

( * ) Notice: Subject to any disclaimer, the term of this patent is extended or adjusted under 35 U.S.C. 154(b) by 999 days.

(21) Appl. No.: 11/696,554

(22) Filed: Apr. 4, 2007

(65) Prior Publication Data

US 2007/0243243 A1 Oct. 18, 2007

Related U.S. Application Data

(60) Provisional application No. 60/789,543, filed on Apr. 4, 2006, provisional application No. 60/812,326, filed on Jun. 9, 2006.

(51) Int. Cl.
| | | |
|---|---|---|
| *A61K 9/28* | (2006.01) | |
| *A61K 9/22* | (2006.01) | |
| *A61K 9/30* | (2006.01) | |
| *A61K 9/52* | (2006.01) | |
| *A61K 31/4439* | (2006.01) | |
| *A61K 9/00* | (2006.01) | |
| *A61K 9/16* | (2006.01) | |
| *A61K 9/20* | (2006.01) | |
| *A61K 9/48* | (2006.01) | |
| *A61K 9/50* | (2006.01) | |
| *A61K 31/4743* | (2006.01) | |
| *A61K 31/616* | (2006.01) | |

(52) U.S. Cl.
CPC ........... *A61K 31/4439* (2013.01); *A61K 9/006* (2013.01); *A61K 9/0056* (2013.01); *A61K 9/1623* (2013.01); *A61K 9/1652* (2013.01); *A61K 9/2077* (2013.01); *A61K 9/2081* (2013.01); *A61K 9/2086* (2013.01); *A61K 9/284* (2013.01); *A61K 9/2846* (2013.01); *A61K 9/4866* (2013.01); *A61K 9/4891* (2013.01); *A61K 9/5042* (2013.01); *A61K 9/5084* (2013.01); *A61K 31/4743* (2013.01); *A61K 31/616* (2013.01)

(58) Field of Classification Search
None
See application file for complete search history.

(56) References Cited

U.S. PATENT DOCUMENTS

| | | | |
|---|---|---|---|
| 4,704,295 A | 11/1987 | Porter et al. | |
| 4,786,505 A | 11/1988 | Lovgren et al. | |
| 5,576,328 A * | 11/1996 | Herbert et al. | 514/301 |
| 5,635,477 A | 6/1997 | Degrado et al. | |
| 5,753,265 A | 5/1998 | Bergstrand et al. | |
| 6,218,403 B1 | 4/2001 | Daste et al. | |
| 6,365,184 B1 | 4/2002 | Depui et al. | |
| 6,544,556 B1 | 4/2003 | Chen et al. | |
| 6,613,354 B2 | 9/2003 | Depui et al. | |
| 6,761,895 B2 | 7/2004 | Sawada et al. | |
| 6,869,615 B2 | 3/2005 | Chen et al. | |
| 7,018,990 B2 | 3/2006 | Wong et al. | |
| 7,029,701 B2 | 4/2006 | Chen | |
| 2003/0129235 A1 | 7/2003 | Chen et al. | |
| 2004/0175427 A1* | 9/2004 | Chen et al. | 424/471 |
| 2005/0147675 A1 | 7/2005 | Petrus | |
| 2006/0177504 A1 | 8/2006 | Sundharadas | |
| 2009/0214602 A1 | 8/2009 | Goldsmith et al. | |

FOREIGN PATENT DOCUMENTS

| | | |
|---|---|---|
| WO | WO 99/032093 A1 | 7/1999 |
| WO | WO 2007/115305 A2 | 10/2007 |

OTHER PUBLICATIONS

Lanas, Angel and James Scheiman. Low-dose aspirin and upper gastrointestinal damage: epidemiology, prevention and treatment. *Curr Med Res Opin* 23(1):163-173 (2007).
Doggrell, Sheila A. Aspirin and esomeprazole are superior to clopidogrel in preventing recurrent ulcer bleeding. *Expert Opin. Pharmacother.* 6(7):1253-6 (2005).
McQuaid, K.R. and Laine, L., Systematic Review and Meta-analysis of Adverse Events of Low-dose Aspirin and Clopidogrel in Randomized Controlled Trials, *American Journal of Medicine* 119:624-638(2006).
Patrono, C., et al., Platelet-Active Drugs: The Relationships Among Dose, Effectiveness, and Side Effects, *Chest* 126(3):234S-264S (2006).
Ng, F.-H., C-Y. Wong, W-H. Chen et al. Clopidogrel plus omeprazole compared with aspirin plus omeprazole for aspirin-induced symptomatic peptic ulcers/erosions with low to moderate bleeding/re-bleeding risk—a single-blind, randomized controlled study. *Aliment. Pharmacol. Ther.* 18:359-65 (2004).
Tateishi, T. et al., Ticlopidine decreases the in vivo activity of CYP2C19 as measured by omeprazole metabolism, *Br J Clinical Pharmacology* 47:454-457 (1999).
Fork, F-T., P. Lafolie, E. Toth et al. Gastroduodenal tolerance of 75 mg clopidogrel versus 325 mg aspirin in healthy volunteers, *Scand J Gastroenterol 2000* (5):464-9 (2000).
Gilard, M., et al., Influence of Omeprazole on the Antiplatelet Action of Clopidogrel Associated to Aspirin, *J Thromb Haemost,* 4:2508-9 (2006).
McEwen, J., et al., Clopidogrel Bioavailability: Absence of Influence of Food or Antacids, *Seminars in Thrombosis and Hemostasis,* 25 Suppl. 2: 47-50 (1999).
Chan, F. K.L., et al., Clopidogrel versus Aspirin and Esomeprazole to Prevent Recurrent Ulcer Bleeding, *N. Engl. J. Med.,* 352:238-44 (2005).
Lai, K-C, et al., Esomeprazole with Aspirin Versus Clopidogrel for Prevention of Recurrent Gastrointestinal Ulcer Complications, *Clin Gastroenterology and Hematology,* 4:860-865 (2006).

(Continued)

Primary Examiner — Nissa Westerberg
(74) Attorney, Agent, or Firm — Sterne, Kessler, Goldstein & Fox P.L.L.C.

(57) ABSTRACT

The present disclosure provides oral dosage forms comprising an antiplatelet agent and an acid inhibitor, as well as methods of treating subjects with an antiplatelet agent and an acid inhibitor.

16 Claims, No Drawings

(56) References Cited

OTHER PUBLICATIONS

Cryer., B., Reducing the Risks of Gastrointestinal Bleeding with Antiplatelet Therapies, *N. Engl. J. Med.*, 352:287-89 (2005).

Chan, F.K., et al., Preventing Recurrent Ulcer Bleeding in Patients on Antiplatelet Therapy: Comparison of 2 Approaches, *JCOM*, 12(3):135-136 (2005).

Chan, F.K., et al., Aspirin plus Esomeprazole reduced recurrent ulcer bleeding more than clopiclogrel in high-risk patients, *CAP J.*, 143(1):9 (2005).

Chan, F.K.L., Management of High-Risk Patients on Non-steroidal Anti-inflammatory Drugs or Aspirin, Drugs, 66 Suppl. 1: 23-28 (2006).

Laheij, R. J. F., et al., Proton-pump Inhibitor Therapy for Acetylsalicylic Acid Associated Upper Gastrointestinal Symptoms: A Randomized Placebo-Controlled Trial, *Aliment Pharmacol Ther.* 18:109-115 (2003).

Study Shows Esomeprazole Reduces Peptic Ulcer Incidence in Patients Taking Low Dose Aspirin, *Doctor's Guide to the Internet*, http://www.pslgroup.com/dg/1F0462.htm, May 30, 2006.

Alexander, W., *Digestive Disease Week, Meeting Highlights, P&T*, 31(7):402-403 (2006).

Bergmann, J.F., et al., Protection Against Aspirin-Induced Gastric Lesions by Lansoprazole: Simultaneous Evaluation of Functional and Morphological Responses, *Clin Pharmacol Ther,* 52(4):413-6(1992).

Low-Dose Aspirin and Stomach Ulcer Medications Better for Heart Patients With Gastrointestinal Complications, (2005).

Chan, F.K.L., et al., Preventing Recurrent Upper Gastrointestinal Bleeding in Patients With Helicobacter Pylori Infection Who Are Taking Low-Dose Aspirin or Naproxen, *N Engl J Med*, 344(13):967-73(2001).

Daneshmend, T.K., et al., Abolition by Omeprazole of Aspirin Induced Gastric Mucosal Injury in Man, *Gut*, 31(5):514-7 (1990).

Inarrea, P., et al., Omeprazole Does Not Interfere With the Antiplatelet Effect of Low-Dose Aspirin in Man, *Scand J Gastroenterol*, 3:242-46 (2000).

Lai, K.C., et al., Lansoprazole for the Prevention of Recurrences of Ulcer Complications From Long-term Low-dose Aspirin Use, *N Engl J Med*, 346(26):2033-38;(2002).

Nefesoglu, F.Z., et al., Interaction of Omeprazole with Enteric-Coated Salicylate Tablets, *Int J Clin Pharmacol Ther,* 36(10):549-53 (1998).

Scheiman, J.M., et al., Omeprazole Ameliorates Aspirin-Induced Gastroduodenal Injury, *Dig Dis Sci*, 39(1):97-103 (1994).

Jacobsen, R.B. and Phillips, B.B., Reducing Clinically Significant Gastrointestinal Toxicity Associated with Nonsteroidal Antiinflammatory Drugs, *Annals of Pharmacotherapy*, 38:1469-1480(2004).

Scheiman, J.M., Nonsteroidal Anti-Inflammatory Drugs, Aspirin, and Gastrointestinal Prophylaxis: An Ounce of Prevention, *Reviews in Gastroenterological Disorders*, 5 Supp. 2:S39-S49(2005).

Cullen, D., et al., Primary Gastroduodenal Prophylaxis With Omeprazole for Non-Steroidal Anti-Inflammatory Drug Users, *Aliment Pharmacol Ther,* 12:135-140 (1998).

Hawkey, C., et al., Improvements with Esomeprazole in Patients With Upper Gastrointestinal Symptoms Taking Non-Steroidal Antiinflammatory Drugs, Including Selective COX-2 Inhibitors, *American J Gastroenterology*, 100:1028-1036(2005).

Hawkey, C.J., et al., Omeprazole Compared With Misoprostol for Ulcers Associated with Nonsteroidal Antiinflammatory Drugs, *N Engl J Med*, 338(11): 727-734 (1998).

Yeomans, N.D., et al., Is Ranitidine Therapy Sufficient for Healing Peptic Ulcers Associated with Non-steroidal Anti-inflammatory Drug Use?, *Int J Clin Pract,* 11:1401-07(2006).

Rey, E., et al., Use of Antisecretory Drugs Among Consumers of Non-steroidal Anti-inflammatory Drugs in the General Population, *Aliment Pharmacol Ther,* 24:1585-1592(2006).

Hawkey, C.J., et al., Efficacy of Esomeprazole for Resolution of Symptoms of Heartburn and Acid Regurgitation in Continuous Users of Nonsteroidal Anti-inflammatory Drugs, *Aliment Pharmacol Ther,* postprint, doi: 10.1111/j.1365-2036.03210.x (2006).

Pilotto, A., et al., Pantoprazole Versus One-Week Helicobacter pylori Eradication Therapy for the Prevention of Acute NSAID-related Gastroduodenal Damage in Elderly Subjects, *Aliment Pharmacol Ther,* 14:1077-1082(2000).

Taha, A.S., et al., Famotidine for the Prevention of Gastric and Duodenal Ulcers Caused by Nonsteroidal Antiinflammatory Drugs, *N Engl J. Med,* 334(22): 1435-1439(2006).

Yeomans, N.D., et al., A Comparison of Omeprazole with Ranitidine for Ulcers Associated with Nonsteroidal Antiinflammatory Drugs, *N Engl J Med*, 338(11)-319-726(2006).

Lanas, A., et al., Low Frequency of Upper Gastrointestinal Complications in a Cohort of High-Risk Patients Taking Low-Dose Aspirin or NSAIDs and Omeprazole, *Scand J. Gastroenterol*, 7:693-700(2003).

Lanas, A., et al., Effect of Antisecretory Drugs and Nitrates on the Risk of Ulcer Bleeding Associated with Nonsteroidal Anti-inflammatory Drugs, Antiplatelet Agents, and Anticoagulants, *Am J Gastroenterol*, 102:1-9(2007).

FDA CDER Application 75-347 for Omeprazole Delayed-release Capsules, Andrx Pharmaceuticals, Nov. 16, 2001.

Schaltenbrand, R., et al, Bioequivalence Between Omeprazole MUPS 20 mg as Tablet and Omeprazole MUPS 20 mg as Tablet Encapsulated in Hard Gelatine *Int J Clin Pharmacol Ther,* 39(10):453-9 (2001).

Cooperative Study, Omeprazole in Duodenal Ulceration: Acid Inhibition, Symptom Relief, Endoscopic Healing, and Recurrence, *British Med. J,* 289:525-528 (1984).

FDA CDER Application 75-410 for Omeprazole Delayed-release Capsules, Kremers Urban Development Company, Nov. 1, 2002.

Liberopoulos, E.N., et al., Upper Gastrointestinal Haemorrhage Complicating Antiplatelet Treatment with Aspirin and/or Clopidogrel: Where Are We Now?, *Platelets,* 17(1):1-6(2006).

Ibanez, L., et al., Upper Gastrointestinal Bleeding Associated with Antiplatelet Drugs, *Aliment Pharmacol Ther,* 23:235-242 (2006).

Joint Meeting of the Arthritis Advisory Committee and the Drug Safety and Risk Management Advisory Committee, Gastrointestinal Effects of NSAIDs and COX-2 Specific Inhibitors: Byron Cryer MD, Feb. 16-18, 2005.

Kam, P.C.A. and Nethery, C.M., The Thienopyridine Derivatives (Platelet Adenosine Diphosphate Receptor Antagonists), Pharmacology and Clinical Developments, *Anaesthesia,* 58:28-35 (2003).

Yeomans, N.D., et al., Prevalence and Incidence of Gastroduodenal Ulcers During Treatment with Vascular Protective Doses of Aspirin, *Aliment Pharmacol Ther,* 22:795-801 (2005).

Ng, F.H., et al., High Incidence of Clopidogrel-Associated Gastrointestinal Bleeding in Patients with Previous Peptic Ulcer Disease, *Aliment Pharmacol Ther,* 18:443-449 (2003).

Almsherqi, et al., Non-bleeding Side Effects of Clopidogrel: Have Large Multi-Center Clinical Trials Underestimated Their Incidence?, *Int J Cardiol,* (2006).

Alvaro-Gracia, J.M., Licofelone—Clinical Update on a Novel LOX/COX Inhibitor for the Treatment of Osteoarthritis, *Rheumatology,* 43: i21-i25 (2004).

Hallas, J., et al., Use of Single and Combined Antithrombotic Therapy and Risk of Serious Upper Gastrointestinal Bleeding: Population Based Case-Control Study, *BMJ,* doi:10.1136 (2006).

Hernandez-Diaz, S. and Garcia Rodriguez, L.A., Cardioprotective Aspirin Users and their Excess Risk of Upper Gastrointestinal Complications, *BMC Medicine,* 4:22-31 (2006).

Garcia Rodriguez, L.A and Hernandez-Diaz, S., Risk of Uncomplicated Peptic Ulcer Among Users of Aspirin and Nonaspirin Nonsteroidal Antiinflarnmatory Drugs, *AM J Epidemiol,* 159(1): 23-31 (2004).

Lanas A., et al., Risk of Upper Gastrointestinal Ulcer Bleeding Associated with Selective Cyclo-oxygenase-2 Inhibitors, Traditional Non-aspirin Non-steroidal Anti-inflammatory Drugs, Aspirin and Combinations, *Gut,* 55:1731-38 (2006).

Lanas, A., et al., Nitrovasodilatols, Low-Dose Aspirin, Other Nonsteroidal Antiinflammatory Drugs, and the Risk of Upper Gastrointestinal Bleeding, *N Engl J Med,* 343:834-9(2000).

(56) References Cited

OTHER PUBLICATIONS

Nielsen, O.H., et al., Systematic Review: Coxibs, Non-steroidal Anti-inflammatory Drugs or No Cyclooxygenase Inhibitors IN Gastroenterological High-Risk Patients?, *Aliment Pharmacol Ther*, 23:27-33 (2006).
Scheiman, J.M., Anti-inflammatory Drugs and GI Safety, *Gastroenterology & Hepatology Annual Review*, 1:36-40 (Jun. 2006).
Vallurupalli, N.G. and Goldhaber; S.Z., Gastrointestinal Complications of Dual Antiplatelet Therapy, *Circulation*, 113:655-58 (2006).
Chan, F.K., et al., Neither a COX-2 Inhibitor nor NSAID Plus PPI Adequately Protected High Risk Patients From Peptic Ulcer Recurrence, Evidence-Based Gastroenterology, 6(1):11-12 (2005).
Marzo, A., et al., Endoscopic Evaluation of the Effects of Indobufen and Aspirin in Healthy Volunteers, *Am J Therapeutics*, 11:98-102 (2004).
Rordorf, C., et al., Gastroduodenal Tolerability of Lumiracoxib vs Placebo and Naproxen: A Pilot Endoscopic Study in Healthy Male Subjects, *Aliment Pharmacol Ther*, 18:533-541 (2003).
Sapoznikov, B., et al., Minidose Aspirin and Gastrointestinal Bleeding—A Retrospective, Case-Control Study in Hospitalized Patients, Digestive Diseases and Sciences, 50(9):1621-24 (2005).
Sheikh, R.A., et al., Endoscopic Evidence of Mucosal Injury in Patients Taking Ticlopidine Compared with Patients Taking Aspirin/Nonsteroidal Antiinflammatory Drugs and Controls, *J Clin Gastroenterol*, 34(5):529-32 (2002).
Serebruany, V.L., Platelet Inhibition with Prasugrel (CS-747) Compared with Clopidogrel in Patients Undergoing Coronary Stenting: the Subset from the JUMBO Study, *PMJ*, 82:404-410 (2006).
"American College of Cardiology/American Heart Association Comment on the FDA Public Health Advisory regarding a drug interaction between clopidogrel and omeprazole," *The American Heart Association*, Nov. 17, 2009, Orlando, FL, Retrieved from <http://americanheart.mediaroom.com/index.php?s=43&item=896&printable>.
"Clopidogrel—Proton Pump Inhibitor Drug Interaction Discussion paper," *NSW Therapeutic Advisory Group*, pp. 1-6, New South Wales, Australia (Feb. 2010).
Allen, C., et al., "Clopidogrel-proton pump inhibitor interaction: a primer for clinicians," *Cardiovasc. Hematol. Disord.—Drug Targets* 10(1): 66-72, Bentham Science Publishers, Netherlands (Mar. 2010; Epub: Dec. 2009).
Bhatt, D.L., et al., "The COGENT Trial," Power Point Presentation Slides, presented at *The Transcatheter Cardiovascular Therapeutics (TCT)* Conference, Slides 1-21, San Francisco, California (Sep. 2009).
Chow, C.K., et al., "Is it safe to use a proton pump inhibitor with clopidogrel?," *Pol. Arch. Med. Wewn.* 119(9): 564-67, Medycyna Praktyczna, Poland (Sep. 2009).
Cuisset, T, et al., "Comparison of omeprazole and pantoprazole influence on a high 150-mg clopidogrel maintenance dose: the PACA (Proton Pump Inhibitors and Clopidogrel Association) prospective randomized study," *J. Am. Coll. Cardiol.* 54(13): 1149-53, Elsevier Biomedical, United States (Sep. 2009).
Depta, J.P. and Bhatt, D.L., "Omeprazole and clopidogrel: Should clinicians be worried?," *Cleve. Clin. J. Med.* 77(2): 113-6, Cleveland Clinic Educational Foundation, United States (Feb. 2010).
Gilard, M., et al., "Influence of omeprazole on the antiplatelet action of clopidogrel associated with aspirin: the randomized, double-blind OCLA (Omeprazole CLopidogrel Aspirin) study," *J. Am. Coll. Cardiol.* 51(3): 256-60, Elsevier Biomedical, United States (Jan. 2008).
Gupta, E., et al., "Risk of Adverse Clinical Outcomes with Concomitant Use of Clopidogrel and Proton Pump Inhibitors Following Percutaneous Coronary Intervention," *Dig. Dis. Sci.*, Springer Science + Business Media, United States (Sep. 2009 [Epub ahead of print]).
Laine, L. and Hennekens, C., "Proton Pump Inhibitor and Clopidogrel Interaction: Fact or Fiction?," *Am. J. Gastroenterol.* 105(1): 34-41, Nature Publishing Group, United States (Jan. 2010; Epub: Nov. 2009).

Norgard, N.B., et al., "Drug-drug interaction between clopidogrel and the proton pump inhibitors," *Ann. Pharmacother.* 43(7): 1266-74, Harvey Whitney Books Co., United States (Jul. 2009; Epub: May 2009).
O'Donoghue, M.L., et al., "Pharmacodynamic effect and clinical efficacy of clopidogrel and prasugrel with or without a proton-pump inhibitor: an analysis of two randomised trials," *Lancet* 374: 989-97, Lancet Publishing Group, England (Sep. 2009; Epub: Aug. 2009).
Sibbing, D., et al., "Impact of proton pump inhibitors on the antiplatelet effects of clopidogrel," *Thromb. Haemost.* 101(4): 714-19, Schattauer, Germany (Apr. 2009).
University of Texas Southwestern Medical Center at Dallas, "Low-Dose Aspirin and Stomach Ulcer Medications Better for Heart Patients With Gastrointestinal Complications," *ScienceDaily*, Feb. 10, 2005. Apr. 13, 2010 <http://www.sciencedaily.com /releases/2005/01/050124004939.htm>.
*Transcatheter Cardiovascular Therapeutics (TCT)* Conference, Partial Program (pp. 1, 4-6, and 94), indicating on p. 94 the session presented by Dr. D.L. Bhatt entitled "COGENT: A Prospective, Randomized, Placebo-Controlled Trial of Omeprazole in Patients Receiving Aspirin and Clopidogrel," San Francisco, California (Sep. 2009).
"Proton Pump Inhibitors and Antiplatelet Drugs Can Be Used Together Following Careful Consideration of the Risks and Benefits," Press release by the *American College of Gastroenterology*, Bethesda, MD, United States, 3 pages (Nov. 8, 2010).
Bhatt, D.L., et al., "Clopidogrel With or Without Omeprazole in Coronary Artery Disease," *N. Engl. J. Med.* 363:1909-1917, Massachusetts Medical Society, United States (Nov. 2010)
Bhatt, D.L, et al., *Protocol* for "Clopidogrel With or Without Omeprazole in Coronary Artery Disease," *N. Engl. J. Med.* 363:1909-1917 (Nov. 2010), 66 pages, Massachusetts Medical Society, United States, available at http://www.nejm.org (last accessed Jul. 13, 2011).
Bhatt, D.L, et al., *Supplementary Appendix* to "Clopidogrel With or Without Omeprazole in Coronary Artery Disease," *N. Engl. J. Med.* 363:1909-1917 (Nov. 2010), 7 pages, Massachusetts Medical Society, United States, available at http://www.nejm.org (last accessed Jul. 13, 2011).
Southworth, M.R. and Temple, R., "Interaction of Clopidogrel and Omeprazole," Letter to the Editor, *N. Engl. J. Med.* 363(20):1977, Massachusetts Medical Society, United States (Nov. 2010).
Moshfegh, K., et al., "Antiplatelet Effects of Clopidogrel Compared with Aspirin After Myocardial Infarction: Enhanced Inhibitory Effects of Combination Therapy," *J. Am. Coll. Cardiol.* 36(3):699-705, Elsevier Science Inc., United States (Sep. 2000).
Tantry, U.S., et al., "Clopidogrel and Proton Pump Inhibitors: Influence of Pharmacological Interactions on Clinical Outcomes and Mechanistic Explanations," *J. Am. Coll. Cardiol. Intv.* 4(4):365-380, Elsevier Inc., United States (Apr. 2011).
Office Action from Chinese Patent Appl. No. 2007800208281, applicant KG Acquisition LLC, mailed Dec. 9, 2010, The Intellectual Property Office of the People's Republic of China, China.
Singapore Examination Report from Application No. 200807475-9, applicant KG Acquisition LLC, mailed Nov. 30, 2010, Danish Patent and Trademark Office, Denmark.
International Search Report for International Application No. PCT/US2009/005671, mailed on Jan. 19, 2010, European Patent Office, The Netherlands.
International Preliminary Report on Patentability with Written Opinion of the International Searching Authority for International Application No. PCT/US2009/005671, mailed on May 5, 2011, The International Bureau of WIPO, Switzerland.
Bergmann, J.F., et al., "Protection against aspirin-induced gastric lesions by lansoprazole: simultaneous evaluation of functional and morphologic responses," *Clin. Pharmacol. Ther.* 52(4):413-6, Natur Pub. Group, United States (Oct. 1992).
Daneshmend, T.K., et al., "Abolition by omeprazole of aspirin induced gastric mucosal injury in man," *Gut* 31(5):514-7, British Medical Assn., England (May 1990).

(56) References Cited

OTHER PUBLICATIONS

Nefesoglu, F.Z., et al., "Interaction of omeprazole with enteric-coated salicylate tablets," *Int. J. Clin. Pharmacol. Ther.* 36(10):549-53, Dustri-Verlag Dr. K. Feistle, Germany (Oct. 1998).

Schaltenbrand, R., et al., "Bioequivalence omeprazole MUPS 20 mg as tablet and omeprazole MUPS 20 mg as tablet encapsulated in a hard gelatine capsule," *Int. J. Clin. Pharmacol. Ther.* 39(10):453-9, Dustri-Verlag Dr. K. Feistle, Germany (Oct. 2001).

Scheiman, J.M., et al., "Omeprazole ameliorates aspirin-induced gastroduodenal injury," *Dig. Dis. Sci,* 39(1):97-103, Plenum Publishing Corporation, United States (Jan. 1994).

Two (2) Letters to the Editor and author response re: Bhatt, D.L., et al., "Clopidogrel With or Without Omeprazole in Coronary Artery Disease," *N. Engl. J. Med.* 363-1909-1917 (Nov. 2010): (1) Sadek, A. and Ford, A.C.; and (2) Juurlink, D., *N. Engl. J. Med.* 364-681-683, Massachusetts Medical Society, United States (Feb. 2011).

\* cited by examiner

ORAL DOSAGE FORMS INCLUDING AN ANTIPLATELET AGENT AND AN ACID INHIBITOR

CROSS-REFERENCE TO RELATED APPLICATIONS

This application claims priority to U.S. Provisional Patent Application Ser. Nos. 60/812,326 filed on Jun. 9, 2006 and 60/789,543 filed on Apr. 4, 2006, which are herein incorporated by reference in their entirety for all purposes.

FIELD OF THE INVENTION

The present teaching relates to co-administering an antiplatelet agent and an acid inhibitor, and to oral dosage forms containing a combination of an antiplatelet agent and an acid inhibitor, for preventing or reducing the gastrointestinal disorders associated with antiplatelet agents.

BACKGROUND OF THE INVENTION

Thrombotic disorders are characterized by formation of a thrombus that obstructs vascular blood flow locally or detaches and embolizes to occlude blood flow downstream. Thrombotic disorders are a major cause of death in the industrialized world. Antiplatelet drugs, which decrease platelet aggregation and inhibit thrombus formation, have been shown to be beneficial in the treatment and prevention of thrombotic disorders.

Presently there are numerous antiplatelet drugs which are widely available, however, most antiplatelet drugs are associated with side effects. For example the administration of antiplatelet agents, such as aspirin and clopidogrel, have been associated with gastrointestinal disorders such as ulcers and gastrointestinal bleeding. In addition, the administration of antiplatelet agents, such as clopidogrel, may make some patients more susceptible to the ulcerogenic effects of ulcerogenic stimuli. It appears that a major factor contributing to the development of these gastrointestinal disorders is the presence of acid in the stomach and upper small intestine. While the mechanisms associated with ulcers and gastrointestinal bleeding are not entirely known, there are many causes of ulcers, including stress, alcohol irritation, *Helicobacter pylori* infection, and the side effects of non-steroid anti-inflammatory drugs such as aspirin, for example. Patients in need of long term antiplatelet drug therapy often may interrupt or not receive such therapy due to gastrointestinal disorders, and as a result, patients are deprived of beneficial antiplatelet drug therapy. There is a need for oral pharmaceutical combination formulations to reduce or eliminate the gastrointestinal disorders associated with use of antiplatelet drugs.

SUMMARY OF THE INVENTION

The present disclosure relates to oral dosage forms comprising in combination an antiplatelet agent and an acid inhibitor, as active agents, termed "actives". In some embodiments, the oral dosage comprises an adenosine diphosphate antagonist in combination with an acid inhibitor. The oral dosage form may comprise a variety of acid inhibitors including, but not limited to, proton pump inhibitors, H₂ blockers, and alkalizing agents. In some embodiments, the oral dosage form and/or active is at least partially enterically coated.

In some embodiments, the oral dosage form comprises clopidogrel or prasugrel in combination with an acid inhibitor. In a more specific embodiment, the oral dosage form comprises clopidogrel or prasugrel in combination with a proton pump inhibitor. In yet another specific embodiment, the oral dosage form comprises clopidogrel or prasugrel in combination with a proton pump inhibitor which is a member selected from omeprazole, esomeprazole, lansoprazole, rabeprazole, and pantoprazole. In yet another specific embodiment, the oral dosage form comprises clopidogrel or prasugrel in combination with omeprazole. In yet another specific embodiment, the oral dosage form is in a single unit. In yet another specific embodiment, the oral dosage form is in two units.

In some embodiments, the oral dosage form comprises aspirin in combination with clopidogrel or prasugrel, in combination with an acid inhibitor. In a more specific embodiment, the oral dosage form comprises aspirin, clopidogrel or prasugrel, and a proton pump inhibitor. In yet another specific embodiment, the oral dosage form comprises clopidogrel or prasugrel, in combination with aspirin and a proton pump inhibitor which is a member selected from omeprazole, esomeprazole, lansoprazole, rabeprazole, and pantoprazole. In yet another specific embodiment, the oral dosage form comprises clopidogrel or prasugrel, in combination with aspirin and omeprazole. The dose of aspirin in said oral dosage form can be selected for its efficacy on platelets.

The oral dosage form can be formulated as capsules, including hard shell capsules and soft shell capsules; tablets, including gastric disintegrating, orally administrable, effervescent and modified release tablets; granules; solutions; suspensions; powders; gels; orally administrable films; and other formulations known in the art. In some embodiments, the oral dosage form includes an enteric coating. In some embodiments, the enteric coating surrounds the acid inhibitor (e.g. in a coating on granules) to isolate it from the antiplatelet agent in the oral dosage form. In other embodiments, the enteric coating surrounds the antiplatelet agent in the oral dosage form. In still other embodiments, the enteric coating surrounds both the acid inhibitor and the antiplatelet agent in the oral dosage form. In some embodiments, the enteric coating surrounds essentially all of the acid inhibitor. In other embodiments, the enteric coating surrounds essentially all of the antiplatelet agent. In still other embodiments, the enteric coating surrounds essentially all of both the acid inhibitor and the antiplatelet agent in the oral dosage form. In other embodiments, the oral dosage form does not include an enteric coating. In other embodiments, the oral dosage form is substantially free of an enteric coating.

The invention also relates to methods of protecting the gastrointestinal tract from side effects associated with antiplatelet therapy using the oral dosage forms described herein. The invention also relates to methods of protecting the gastrointestinal tract from side effects associated with antiplatelet therapy by co-administering an antiplatelet agent and an acid inhibitor. These and other features of the present teachings are set forth herein.

DETAILED DESCRIPTION OF THE INVENTION

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

DEFINITIONS

As used herein, the following terms have the following meanings:

The phrase "acid inhibitor" means an agent capable of inhibiting or decreasing gastric acid secretion and includes the decreasing or neutralizing of gastric acid. The term "acid inhibitor" includes, but is not limited to, proton pump inhibitors, including reversible proton pump inhibitors and irreversible proton pump inhibitors, $H_2$ blockers, and alkalizing agents.

The phrase "alkalizing agent", means a pharmaceutically acceptable excipient, which includes antacids, which will raise the pH in a subject's stomach after being orally administered to the subject.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation. For antiplatelet agents (e.g., clopidogrel) or aspirin, a therapeutically effective amount is the amount sufficient to reduce atherothrombotic events in a patient (e.g. to an extent similar to the reduction caused by clopidogrel). For a proton pump inhibitor (PPI), a therapeutically effective amount is the amount considered to be therapeutically useful for known PPIs, e.g. omeprazole, typically an amount sufficient to reduce gastric acid output by an average of at least 20%, at peak effect of the PPI, across a patient population.

The phrase "antiplatelet agent" refers to any compound, other than nonsteroidal anti-inflammatory agents (NSAIDs) such as aspirin, which inhibits activation, aggregation, and/or adhesion of platelets, and is intended to include all pharmaceutically acceptable salts, prodrugs e.g., esters and solvate forms, including hydrates, of compounds which have the activity, compounds having one or more chiral centers may occur as racemates, racemic mixtures and as individual diastereomers or enantiomers with all such isomeric forms and mixtures thereof being included, any crystalline polymorphs, co-crystals and the amorphous form are intended to be included.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical composition administered to a subject via the oral cavity, in which one or more antiplatelet agents and one or more acid inhibitors are administered concurrently in combination, optionally with one or more additional drugs. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be ingested which comprise the oral dosage form. In some embodiments, the oral dosage form includes an antiplatelet agent and an acid inhibitor contained within one capsule. This is a single unit, whether or not the interior of the capsule includes multiple discrete granules of active ingredient. For example, in some embodiments, the oral dosage form includes an antiplatelet agent, an acid inhibitor and, optionally, aspirin contained within one capsule. This is also a single unit. In some embodiments, the oral dosage form includes an antiplatelet agent and aspirin in one capsule, and an acid inhibitor in a second capsule. This is also a two unit oral dosage form, such as two capsules or tablets, and so such units are contained in a single package. Thus the term 'unit' refers to the object which the patient ingests, not to the interior components of the object.

The phrases "active ingredient", "therapeutic agent", "active", or "active agent" mean a chemical entity which can be effective in treating a targeted disorder, disease or condition.

The phrase "therapeutically effective amount" means a sufficient quantity of a therapeutic agent such as an antiplatelet agent or an acid inhibitor which is effective in treating the targeted disorder, disease or condition.

The term "substrates" means pharmaceutically acceptable particulate materials such as beads, particles, granules, pellets, and the like, in an oral dosage form.

The term, "substantially free", as used herein, refers to a composition which contains none of the substance or less than a therapeutically effective amount of the substance for any known purpose for which the composition is intended.

The term, "essentially all", as used herein, refers to a composition in which a member selected from at least 90%, at least 93%, at least 95%, at least 98%, and at least 99% of the members of the composition have the trait which is described. For example, if "essentially all" of the acid inhibitor in a composition is enterically coated, then at least 90%, or at least 93%, or at least 95%, or at least 98%, or at least 99% of the acid inhibitor molecules of the composition are contained within an enteric coat.

The term, "gastrointestinal disorder", as used herein, refers to those conditions which afflict the gastrointestinal system of a subject/patient. Examples of a gastrointestinal disorder include, without limitation, the presence and/or secretion of excess acid, gastric bleeding, pre-ulcer lesions and ulcers, such as peptic ulcers including gastric ulcers and duodenal ulcers, bleeding peptic ulcers, stress ulcers, stomal ulcers, refractory ulcers, esophageal ulcers, bacterial-induced ulcers, such as *H. pylori*, fungal-induced ulcers, viral-induced ulcers, and the like.

I. Oral Dosage Forms

The present disclosure provides oral dosage forms and uses thereof for inhibiting platelet aggregation, treating disease which arises from prothrombotic and thrombotic states in which the coagulation cascade is activated, reducing the risk of cardiovascular disease, and reducing the gastrointestinal disorders associated with antiplatelet agents.

The oral dosage forms provided herein can be administered in any form suitable for oral administration. The dosage forms comprise an antiplatelet agent in combination with an acid inhibitor. In an exemplary embodiment, the oral dosage form comprises a therapeutically effective amount of a first active ingredient, wherein said first active ingredient is an antiplatelet agent, and a therapeutically effective amount of a second active ingredient, wherein said second active ingredient is an acid inhibitor. In an exemplary embodiment, the oral dosage form does not include aspirin. In an exemplary embodiment, the oral dosage form is substantially free of aspirin. In another exemplary embodiment, the oral dosage form does not include a non-aspirin NSAID. In another exemplary embodiment, the oral dosage form is substantially free of a non-aspirin NSAID. In a further exemplary embodiment, the oral dosage form does not further comprise a therapeutically effective amount of a third active ingredient. In a further exemplary embodiment, the oral dosage form is a single unit. In a further exemplary embodiment, the oral dosage form is in two units, wherein a first unit comprises said antiplatelet agent and a second unit comprises said acid inhibitor.

I. a) Antiplatelet Agents

Any compound having platelet aggregation inhibitor-like activity can be used in the present oral dosage forms. Non-limiting examples of antiplatelet agents that may be used in the oral dosage forms of the present invention include adenosine diphosphate (ADP) antagonists or $P_2Y_{12}$ antagonists, phosphodiesterase (PDE) inhibitors, adenosine reuptake inhibitors, Vitamin K antagonists, heparin, heparin analogs, direct thrombin inhibitors, glycoprotein IIB/IIIA inhibitors, anti-clotting enzymes, as well as pharmaceutically acceptable salts, isomers, enantiomers, polymorphic crystal forms including the amorphous form, solvates, hydrates, co-crystals, complexes, active metabolites, active derivatives and modifications, pro-drugs thereof, and the like. With the exception of the Examples section, reference herein to an antiplatelet agent or to a specific antiplatelet drug compound, e.g. clopidogrel, encompasses the agent or drug itself and active forms of the agent or drug such as set forth in the previous sentence. As used herein, the term "antiplatelet agent" excludes aspirin and non-aspirin NSAIDs.

ADP antagonists or $P_2Y_{12}$ antagonists block the ADP receptor on platelet cell membranes. This $P_2Y_{12}$ receptor is important in platelet aggregation, the cross-linking of platelets by fibrin. The blockade of this receptor inhibits platelet aggregation by blocking activation of the glycoprotein IIb/IIIa pathway. In an exemplary embodiment, the antiplatelet agent is an ADP antagonist or $P_2Y_{12}$ antagonist. In another exemplary embodiment, the antiplatelet agent is a thienopyridine. In another exemplary embodiment, the ADP antagonist or $P_2Y_{12}$ antagonist is a thienopyridine.

In another exemplary embodiment, the ADP antagonist or $P_2Y_{12}$ antagonist is a member selected from sulfinpyrazone, ticlopidine, clopidogrel, prasugrel, R-99224 (an active metabolite of prasugrel, supplied by Sankyo), R-1381727, R-125690 (Lilly), C-1330-7, C-50547 (Millennium Pharmaceuticals), INS-48821, INS-48824, INS-446056, INS-46060, INS-49162, INS-49266, INS-50589 (Inspire Pharmaceuticals) and Sch-572423 (Schering Plough). In another exemplary embodiment, the ADP antagonist or $P_2Y_{12}$ antagonist is ticlopidine hydrochloride (TICLID™). In another exemplary embodiment, the ADP antagonist or $P_2Y_{12}$ antagonist is a member selected from sulfinpyrazone, ticlopidine, AZD6140, clopidogrel, prasugrel and mixtures thereof. In another exemplary embodiment, the ADP antagonist or $P_2Y_{12}$ antagonist is clopidogrel. In another exemplary embodiment, the therapeutically effective amount of clopidogrel is from about 50 mg to about 100 mg. In another exemplary embodiment, the therapeutically effective amount of clopidogrel is from about 65 mg to about 80 mg. In another exemplary embodiment, the ADP antagonist or $P_2Y_{12}$ antagonist is a member selected from clopidogrel bisulfate (PLAVIX™), clopidogrel hydrogen sulphate, clopidogrel hydrobromide, clopidogrel mesylate, cangrelor tetrasodium (AR-09931 MX), ARL67085, AR-C66096 AR-C 126532, and AZD-6140 (AstraZeneca). In another exemplary embodiment, the ADP antagonist or $P_2Y_{12}$ antagonist is prasugrel. In another exemplary embodiment, the therapeutically effective amount of prasugrel is from about 1 mg to about 20 mg. In another exemplary embodiment, the therapeutically effective amount of clopidogrel is from about 4 mg to about 11 mg. In another exemplary embodiment, the ADP antagonist or $P_2Y_{12}$ antagonist is a member selected from clopidogrel, ticlopidine, sulfinpyrazone, AZD6140, prasugrel and mixtures thereof.

A PDE inhibitor is a drug that blocks one or more of the five subtypes of the enzyme phosphodiesterase (PDE), preventing the inactivation of the intracellular second messengers, cyclic adenosine monophosphate (cAMP) and cyclic guanosine monophosphate (cGMP), by the respective PDE subtype(s). In an exemplary embodiment, the antiplatelet agent is a PDE inhibitor. In an exemplary embodiment, the antiplatelet agent is a selective cAMP PDE inhibitor. In an exemplary embodiment, the PDE inhibitor is cilostazol (Pletal™).

Adenosine reuptake inhibitors prevent the cellular reuptake of adenosine into platelets, red blood cells and endothelial cells, leading to increased extracellular concentrations of adenosine. These compounds inhibit platelet aggregation and cause vasodilation. In an exemplary embodiment, the antiplatelet agent is an adenosine reuptake inhibitor. In an exemplary embodiment, the adenosine reuptake inhibitor is dipyridamole (Persantine™).

Vitamin K inhibitors are given to people to stop thrombosis (blood clotting inappropriately in the blood vessels). This is useful in primary and secondary prevention of deep vein thrombosis, pulmonary embolism, myocardial infarctions and strokes in those who are predisposed. In an exemplary embodiment, the anti-platelet agent is a Vitamin K inhibitor. In an exemplary embodiment, the Vitamin K inhibitor is a member selected from acenocoumarol, clorindione, dicumarol (Dicoumarol), diphenadione, ethyl biscoumacetate, phenprocoumon, phenindione, tioclomarol and warfarin.

Heparin is a biological substance, usually made from pig intestines. It works by activating antithrombin III, which blocks thrombin from clotting blood. In an exemplary embodiment, the antiplatelet agent is heparin or a prodrug of heparin. In an exemplary embodiment, the antiplatelet agent is a heparin analog or a prodrug of a heparin analog. In an exemplary embodiment, the heparin analog a member selected from Antithrombin III, Bemiparin, Dalteparin, Danaparoid, Enoxaparin, Fondaparinux (subcutaneous), Nadroparin, Parnaparin, Reviparin, Sulodexide, and Tiniaparin.

Direct thrombin inhibitors (DTIs) are a class of medication that act as anticoagulants (delaying blood clotting) by directly inhibiting the enzyme thrombin. In an exemplary embodiment, the antiplatelet agent is a DTI. In another exemplary embodiment, the DTI is univalent. In another exemplary embodiment, the DTI is bivalent. In an exemplary embodiment, the DTI is a member selected from hirudin, bivalirudin (IV), lepirudin, desirudin, argatroban (IV), dabigatran, dabigatran etexilate (oral formulation), melagatran, ximelagatran (oral formulation but liver complications) and prodrugs thereof.

Glycoprotein IIB/IIIA inhibitors work by inhibiting the GpIIb/IIIa receptor on the surface of platelets, thus preventing platelet aggregation and thrombus formation. In an exemplary embodiment, the antiplatelet agent is a glycoprotein IIB/IIIA inhibitor. In an exemplary embodiment, the glycoprotein IIB/IIIA inhibitor is a member selected from abciximab, eptifibatide, tirofiban and prodrugs thereof. Since these drugs are only administered intravenously, a prodrug of a glycoprotein IIB/IIIA inhibitor is useful for oral administration.

Anti-clotting enzymes may also be used in the invention. In an exemplary embodiment, the antiplatelet agent is an anti-clotting enzyme which is in a form suitable for oral administration. In another exemplary embodiment, the anti-clotting enzyme is a member selected from Alteplase, Ancrod, Anistreplase, Brinase, Drotrecogin alfa, Fibrinolysin, Protein C, Reteplase, Saruplase, Streptokinase, Tenecteplase, Urokinase.

In an exemplary embodiment, the anti-platelet agent is a member selected from aloxiprin, beraprost, carbasalate calcium, cloricromen, defibrotide, ditazole, epoprostenol, indobufen, iloprost, picotamide, rivaroxaban (oral FXa inhibitor) treprostinil, triflusal, or prodrugs thereof.

I. b) Acid Inhibitors

Any compound having acid inhibitor-like activity can be used as an acid inhibitor in the present oral dosage forms. Non-limiting examples of acid inhibitors that may be used in the oral dosage form a of the present invention include proton pump inhibitors, $H_2$ blockers and alkalizing agents.

In an exemplary embodiment, the acid inhibitor has proton pump inhibitor activity, including both reversible and irreversible proton pump inhibitors. Suitable non-limiting examples of proton pump inhibitors include omeprazole (Prilosec™), esomeprazole (Nexium™), lansoprazole (Prevacid™), leminoprazole, rabeprazole (Aciphex™), pantoprazole (Protonix™), hydroxyomeprazole, pariprazole, dontoprazole, habeprazole, periprazole, ransoprazole, tenatoprazole (benatoprazole), ilaprazole, proomeprazole, IY-81149, AZD-8065, hydroxylansoprazole, including pharmaceutically acceptable salts, isomers, enantiomers, derivatives, prodrugs, crystal polymorphs, amorphous modifications, solvates and hydrates, co-crystals, complexes and combinations thereof. With the exception of the Examples section, reference herein to an acid inhibitor or to a specific acid inhibitor compound, e.g. omeprazole, encompasses the agent or drug itself and active forms of the agent or drug such as set forth in the previous sentence.

In another exemplary embodiment, the proton pump inhibitor is a member selected from omeprazole, rabepazole, pantoprazole, esomeprazole and lansoprazole. In another exemplary embodiment, the proton pump inhibitor is a member selected from omeprazole and esomeprazole. In another exemplary embodiment, the proton pump inhibitor is a member selected from omeprazole and esomeprazole, and the therapeutically effective amount of said second ingredient is from about 10 mg to about 80 mg. In another exemplary embodiment, the therapeutically effective amount of omeprazole is from about 10 mg to about 80 mg, and the therapeutically effective amount of esomeprazole is from about 10 mg to about 40 mg.

In addition to compounds described above, the acid inhibitor may include compounds which reversibly bind to the enzyme responsible for gastric acid secretion, $H^+/K^+$ ATPase, the so called "reversible proton pump inhibitors." Suitable non-limiting examples include Sch-28080 (Schering Plough); Sch-32651 (Schering Plough), AZD-0865, AR-H047108, CS-526, pumaprazole, revaprazan (see WO 1998018784; U.S. Pat. No. 6,252,076; U.S. Pat. No. 5,990, 311 and U.S. Pat. No. 5,750,531) soraprazan (see WO9605177 and WO9605199), H-335/25 (AstraZeneca) and SK&F-96067 (GlaxoSmithKline), and the reversible proton pump inhibitors disclosed, for example, in the documents U.S. Pat. No. 4,833,149, U.S. Pat. No. 5,041,442, U.S. Pat. No. 4,464,372, U.S. Pat. No. 6,132,768, including pharmaceutically acceptable salts, isomers, enantiomers, polymorphs, solvates, hydrates, amorphous modifications, co-crystals, derivatives, and combinations thereof.

Additional suitable non-limiting examples of acid inhibitors include SK&F-95601, SK&F-96067 and SK&F-97574 (GlaxoSmithKline), NC-I300 and NC-1300-B (Nippon Chemiphar); Hoe-73I (Saviprazole) (Sanofi-Aventis); IY-81149 (Ilaprazole); H-405/02 (AstraZeneca); CS-526 and R-105266 (Novartis; Sankyo; Ube); TY-11345 or neprazole sodium (Toa Eiyo); BY-841 (Altana Pharma), and TU-199 (TAP; Takeda), including pharmaceutically acceptable salts, isomers, enantiomers, polymorphs, amorphous modifications, co-crystals, solvates, hydrates and derivatives thereof, and combinations thereof.

The acid inhibitor may also comprise any compound having $H_2$ blocker or $H_2$ antagonist activity. Suitable non-limiting examples include ranitidine, cimetidine, nizatidine, famotidine, roxatidine as well as pharmaceutically acceptable salts, isomers, polymorphs, amorphous modifications, co-crystals, derivatives, prodrugs, enantiomers, solvates, hydrates, and combinations thereof.

The acid inhibitor of the oral dosage forms may also comprise any compound having alkalizing activity. Alkalizing agents of the present disclosure raise the pH of acidic aqueous solutions and include, for example, antacids as well as other pharmaceutically acceptable organic and inorganic bases, salts of strong organic and inorganic acids, salts of weak organic and inorganic acids, and buffers.

Suitable non-limiting examples of alkalizing agents are basic compounds, e.g. having a pH in an aqueous solution greater than about pH 7, and include, but are not limited to metallic salts e.g. aluminum salts such as aluminum carbonate (Basajel), magnesium aluminum silicate; magnesium salts such as magnesium carbonate, magnesium trisilicate, magnesium aluminum silicate, magnesium stearate; calcium salts such as calcium carbonate; bicarbonates such as calcium bicarbonate and sodium bicarbonate; phosphates such as monobasic calcium phosphate, dibasic calcium phosphate, dibasic sodium phosphate, tribasic sodium phosphate (TSP), dibasic potassium phosphate, tribasic potassium phosphate; metal hydroxides such as aluminum hydroxide, sodium hydroxide, mid magnesium hydroxide; metal oxides such as magnesium oxide; N-methyl glucamine; arginine and salts thereof; hydrotalcite (Talcid); Bismuth salts such as bismuth subsalicylate (PeptoBismol); magaldrate; simethicone (Pepsil); amines such as monoethanolamine, diethanolamine, triethanolamine, and tris(hydroxymethyl)aminomethane (TRIS); and combinations thereof.

Reference herein to an acid inhibitor, to different classes of acid inhibitors, e.g. protein pump inhibitors, and to specific compounds within such classes, encompasses the inhibitors, classes, and compounds as well as pharmaceutically acceptable salts, isomers, enantiomers, polymorphic crystal forms including the amorphous form, solvates, hydrates, co-crystals, complexes, active metabolites, active derivatives and modifications, pro-drugs thereof, and the like. Reference herein to an acid inhibitor or to a specific acid inhibitor, e.g. omeprazole, encompasses the agent or drug itself and active forms of the agent or drug such as set forth in the previous sentence, I. c) Specific Combinations of Antiplatelet Agents and Acid Inhibitors In an exemplary embodiment, the invention provides a single unit oral dosage form comprising a therapeutically effective amount of an adenosine diphosphate antagonist, and a therapeutically effective amount of an irreversible proton pump inhibitor. In an exemplary embodiment, the invention provides a single unit oral dosage form comprising a therapeutically effective amount of an adenosine diphosphate antagonist, and a therapeutically effective amount of a reversible proton pump inhibitor. In an exemplary embodiment, the invention provides a single unit oral dosage form comprising a therapeutically effective amount of an adenosine diphosphate antagonist, and a therapeutically effective amount of an H$_2$ blocker. In an exemplary embodiment, the invention provides a single unit oral dosage form comprising a therapeutically effective amount of an adenosine diphosphate antagonist, and a therapeutically effective amount of an alkalizing agent. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiments the single unit oral dosage form described in this paragraph further comprises a therapeutically effective amount of a non-aspirin NSAID.

I. c1) Specific Combinations of Adenosine Diphosphate Inhibitors and Proton Pump Inhibitors In an exemplary embodiment, the invention provides a single unit oral dosage form comprising a therapeutically effective amount of a member selected from clopidogrel, prasugrel and mixtures thereof, and a therapeutically effective amount of a proton pump inhibitor. In another exemplary embodiment, the invention provides a single unit oral dosage form comprising a therapeutically effective amount of a member selected from clopidogrel, prasugrel and mixtures thereof, and a therapeutically effective amount of an irreversible proton pump inhibitor. In another exemplary embodiment, the invention provides a single unit oral dosage form comprising a therapeutically effective amount of a member selected from clopidogrel, prasugrel and mixtures thereof, and a therapeutically effective amount of a reversible proton pump inhibitor. In a further exemplary embodiment, the invention provides a single unit oral dosage form comprising a therapeutically effective amount of a member selected from clopidogrel, prasugrel and mixtures thereof, and a therapeutically effective amount of an H$_2$ blocker. In an exemplary embodiment, the invention provides a single unit oral dosage form comprising a therapeutically effective amount of a member selected from clopidogrel, prasugrel and mixtures thereof, and a therapeutically effective amount of an alkalizing agent. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

I. c2) Specific Combinations of Antiplatelet Agents with Specific Proton Pump Inhibitors In an exemplary embodiment, the invention provides a single unit oral dosage form comprising a therapeutically effective amount of an antiplatelet agent and a therapeutically effective amount of a proton pump inhibitor. In an exemplary embodiment, the proton pump inhibitor is omeprazole. In another exemplary embodiment, omeprazole is present in an amount of between about 10 mg and about 40 mg. In another exemplary embodiment, omeprazole is present in an amount of about 20 mg. In an exemplary embodiment, the proton pump inhibitor is esomeprazole. In another exemplary embodiment, esomeprazole is present in an amount of between about 10 mg and about 40 mg. In another exemplary embodiment, esomeprazole is present in an amount of about 20 mg. In an exemplary embodiment, the proton pump inhibitor is lansoprazole. In another exemplary embodiment, lansoprazole is present in an amount of between about 15 mg and about 60 mg. In another exemplary embodiment, lansoprazole is present in an amount of about 15 mg to about 30 mg. In an exemplary embodiment, the proton pump inhibitor is rabeprazole. In another exemplary embodiment, rabeprazole is present in an amount of between about 10 mg and about 60 mg. In another exemplary embodiment, rabeprazole is present in an amount of about 20 mg. In an exemplary embodiment, the proton pump inhibitor is pantoprazole. In another exemplary embodiment, pantoprazole is present in an amount of between about 10 mg and about 40 mg. In another exemplary embodiment, pantoprazole is present in an amount of about 20 mg to about 40 mg. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

I. c3) Specific Combinations of Clopidogrel or Prasugrel and Proton Pump Inhibitors In an exemplary embodiment, the invention provides a single unit oral dosage form comprising a therapeutically effective amount of a member selected from clopidogrel, prasugrel and mixtures thereof, and a therapeutically effective amount of a proton pump inhibitor ("PPI"), selected from omeprazole, esomeprazole, lansoprazole, leminoprazole, rabeprazole, pantoprazole, hydroxyomeprazole, pariprazole, dontoprazole, habeprazole, periprazole, ransoprazole, and tenatoprazole (benatoprazole) and mixtures thereof. In an exemplary embodiment, the invention provides a single unit oral dosage form comprising a therapeutically effective amount of clopidogrel and a therapeutically effective amount of one or more of the PPIs set forth above. In another exemplary embodiment, the invention provides a single unit oral dosage form comprising a therapeutically effective amount of prasugrel and a therapeutically effective amount of one or more of the PPIs set forth above. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

In an exemplary embodiment, the invention provides a single unit oral dosage form comprising a therapeutically effective amount of a member selected from clopidogrel, prasugrel and mixtures thereof, and a therapeutically effective amount of a PPI selected from omeprazole, esomeprazole, lansoprazole, leminoprazole and mixtures thereof. In an exemplary embodiment, the invention provides a single unit oral dosage form comprising a therapeutically effective amount of clopidogrel, and a therapeutically effective amount of a PPI selected from omeprazole, esomeprazole, lansoprazole, leminoprazole and mixtures thereof. In an exemplary embodiment, the invention provides a single unit oral dosage form comprising a therapeutically effective amount of prasugrel, and a therapeutically effective amount of a PPI selected from omeprazole, esomeprazole, lansoprazole, leminoprazole and mixtures thereof. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

In an exemplary embodiment, the invention provides a single unit oral dosage form comprising a therapeutically effective amount of a member selected from clopidogrel, prasugrel and mixtures thereof, and a therapeutically effective amount of a PPI selected from omeprazole, esomeprazole and mixtures thereof. In an exemplary embodiment, the invention provides a single unit oral dosage form comprising a therapeutically effective amount of clopidogrel, and a therapeutically effective amount of a PPI selected from omeprazole, esomeprazole and mixtures thereof. In an exemplary embodiment, the invention provides a single unit oral dosage form comprising a therapeutically effective amount of clopidogrel, and a therapeutically effective amount of omeprazole. In an exemplary embodiment, the invention provides a single unit oral dosage form comprising a therapeutically effective amount of prasugrel, and a therapeutically effective amount of a PPI selected from omeprazole. In an exemplary embodiment, the invention provides a single unit oral dosage form comprising a therapeutically effective amount of clopidogrel, and a therapeutically effective amount of esomeprazole. In an exemplary embodiment, the invention provides a single unit oral dosage form comprising a therapeutically effective amount of prasugrel, and a therapeutically effective amount of a PPI selected from esomeprazole. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

In an exemplary embodiment, the invention provides a single unit oral dosage form comprising a therapeutically effective amount of clopidogrel and a therapeutically effective amount of a member selected from omeprazole, esomeprazole, lansoprazole, rabeprazole, pantoprazole and mixtures thereof. In an exemplary embodiment, the invention provides a single unit oral dosage form comprising between about 50 mg and about 100 mg of clopidogrel and between about 10 mg and about 40 mg of omeprazole. In an exemplary embodiment, the invention provides a single unit oral dosage form comprising between about 50 mg and about 100 mg of clopidogrel and between about 10 mg and about 40 mg of esomeprazole. In an exemplary embodiment, the invention provides a single unit oral dosage form comprising between about 50 mg and about 100 mg of clopidogrel and between about 15 mg and about 30 mg of lansoprazole. In an exemplary embodiment, the invention provides a single unit oral dosage form comprising between about 50 mg and about 100 mg of clopidogrel and between about 10 mg and about 60 mg of rabeprazole. In an exemplary embodiment, the invention provides a single unit oral dosage form comprising between about 50 mg and about 100 mg of clopidogrel and between about 10 mg and about 40 mg of pantoprazole. In another exemplary embodiment, the amount of clopidogrel in the single unit oral dosage forms described in this paragraph is between about 65 mg and about 80 mg. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

In an exemplary embodiment, the invention provides a single unit oral dosage form comprising a therapeutically effective amount of prasugrel and a therapeutically effective amount of a member selected from omeprazole, esomeprazole, lansoprazole, rabeprazole, pantoprazole and mixtures thereof. In an exemplary embodiment, the invention provides a single unit oral dosage form comprising between about 1 mg and about 20 mg of prasugrel and between about 10 mg and about 40 mg of omeprazole. In an exemplary embodiment, the invention provides a single unit oral dosage form comprising between about 1 mg and about 20 mg of prasugrel and between about 10 mg and about 40 mg of esomeprazole. In an exemplary embodiment, the invention provides a single unit oral dosage form comprising between about 1 mg and about 20 mg of prasugrel and between about 15 mg and about 30 mg of lansoprazole. In an exemplary embodiment the invention provides a single unit oral dosage form comprising between about 1 mg and about 20 mg of prasugrel and between about 10 mg and about 60 mg of rabeprazole. In an exemplary embodiment, the invention provides a single unit oral dosage form comprising between about 1 mg and about 20 mg of prasugrel and between about 10 mg and about 40 mg of pantoprazole. In another exemplary embodiment, the amount of prasugrel in the single unit oral dosage forms described in this paragraph is between about 4 mg and about 11 mg. In another exemplary embodiment, the single unit oral dosage from described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

I. c4) Specific Combinations of Antiplatelet Agents with Specific $H_2$ Inhibitors In an exemplary embodiment, the invention provides a single unit oral dosage form comprising a therapeutically effective amount of an antiplatelet agent and a therapeutically effective amount of an $H_2$ blocker. In an exemplary embodiment, the $H_2$ blocker is cimetidine. In another exemplary embodiment, cimetidine is present in an amount of between about 300 mg and about 800 mg. In an exemplary embodiment, the $H_2$ blocker is famotidine. In another exemplary embodiment, famotidine is present in an amount of between about 20 mg and about 80 mg. In another exemplary embodiment, famotidine is present in an amount of about 40 mg. In an exemplary embodiment, the $H_2$ blocker is nizatidine. In another exemplary embodiment, nizatidine is present in an amount of between about 150 mg and about 450 mg. In another exemplary embodiment, nizatidine is present in an amount of about 300 mg. In an exemplary embodiment, the $H_2$ blocker is ranitidine. In another exemplary embodiment, ranitidine is present in an amount of between about 150 mg and about 450 mg. In another exemplary embodiment, ranitidine is present in an amount of about 300 mg. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

I. c5) Specific Combinations of Clopidogrel or Prasugrel and $H_2$ Blockers

In an exemplary embodiment, the invention provides a single unit oral dosage form comprising a therapeutically effective amount of a member selected from clopidogrel, prasugrel and mixtures thereof, and a therapeutically effective amount of a member selected from ranitidine, cimetidine, nizatidine, famotidine, roxatidine and mixtures thereof. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

In an exemplary embodiment, the invention provides a single unit oral dosage form comprising a therapeutically effective amount of a member selected from clopidogrel, prasugrel and mixtures thereof, and a therapeutically effective amount of a member selected from ranitidine, cimetidine, nizatidine, famotidine, roxatidine and mixtures thereof. In an exemplary embodiment, the invention provides a single unit oral dosage form comprising a therapeutically effective amount of clopidogrel, and a therapeutically effective amount of a member selected from ranitidine, cimetidine, nizatidine, famotidine, roxatidine and mixtures thereof. In an exemplary embodiment, the invention provides a single unit oral dosage form comprising a therapeutically effective amount of prasugrel, and a therapeutically effective amount of a member selected from ranitidine, cimetidine, nizatidine, famotidine, roxatidine and mixtures thereof. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

In an exemplary embodiment, the invention provides a single unit oral dosage form comprising a therapeutically effective amount of a member selected from clopidogrel, prasugrel and mixtures thereof, and a therapeutically effective amount of a member selected from ranitidine, cimetidine, and mixtures thereof. In an exemplary embodiment, the invention provides a single unit oral dosage form comprising a therapeutically effective amount of clopidogrel, and a therapeutically effective amount of a member selected from ranitidine, cimetidine and mixtures thereof. In an exemplary embodiment, the invention provides a single unit oral dosage form comprising a therapeutically effective amount of prasugrel, and a therapeutically effective amount of a member selected from ranitidine, cimetidine and mixtures thereof. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

In an exemplary embodiment, the invention provides a single unit oral dosage form comprising a therapeutically effective amount of clopidogrel and a therapeutically effective amount of a member selected from ranitidine, cimetidine, nizatidine, famotidine, roxatidine and mixtures thereof. In an exemplary embodiment, the invention provides a single unit oral dosage form comprising between about 50 mg and about 100 mg of clopidogrel and between about 300 mg and about 800 mg of cimetidine. In an exemplary embodiment, the invention provides a single unit oral dosage form comprising between about 50 mg and about 100 mg of clopidogrel and between about 20 mg and about 80 mg of famotidine. In an exemplary embodiment, the invention provides a single unit oral dosage form comprising between about 50 mg and about 100 mg of clopidogrel and between about 150 mg and about 300 mg of nizatidine. In an exemplary embodiment, the invention provides a single unit oral dosage form comprising between about 50 mg and about 100 mg of clopidogrel and between about 150 mg and about 300 mg of ranitidine. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

In an exemplary embodiment, the invention provides a single unit oral dosage form comprising a therapeutically effective amount of prasugrel and a therapeutically effective amount of a member selected from ranitidine, cimetidine, nizatidine, famotidine, roxatidine and mixtures thereof. In an exemplary embodiment, the invention provides a single unit oral dosage form comprising between about 1 mg and about 20 mg of prasugrel and between about 300 mg and about 800 mg of cimetidine. In an exemplary embodiment, the invention provides a single unit oral dosage form comprising between about 1 mg and about 20 mg of prasugrel and between about 20 mg and about 80 mg of famotidine. In an exemplary embodiment, the invention provides a single unit oral dosage form comprising between about 1 mg and about 20 mg of prasugrel and between about 150 mg and about 300 mg of nizatidine. In an exemplary embodiment, the invention provides a single unit oral dosage form comprising between about 1 mg and about 20 mg of prasugrel and between about 150 mg and about 300 mg of ranitidine. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

I. c6) Specific Combinations of Phosphodiesterase Inhibitors with Acid Inhibitors In an exemplary embodiment, the invention provides a single unit oral dosage form comprising a therapeutically effective amount of a phosphodiesterase inhibitor, and a therapeutically effective amount of an acid inhibitor. In an exemplary embodiment, the invention provides a single unit oral dosage form comprising a therapeutically effective amount of a phosphodiesterase inhibitor, and a therapeutically effective amount of an irreversible proton pump inhibitor. In an exemplary embodiment, the invention provides a single unit oral dosage form comprising a therapeutically effective amount of a phosphodiesterase inhibitor, and a therapeutically effective amount of a reversible proton pump inhibitor. In an exemplary embodiment, the invention provides a single unit oral dosage form comprising a therapeutically effective amount of a phosphodiesterase inhibitor, and a therapeutically effective amount of an $H_2$ blocker. In an exemplary embodiment, the invention provides a single unit oral dosage form comprising a therapeutically effective amount of a phosphodiesterase inhibitor, and a therapeutically effective amount of an alkalizing agent. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

I. c7) Specific Combinations of Adenosine Reuptake Inhibitors with Acid Inhibitors In an exemplary embodiment, the invention provides a single unit oral dosage form comprising a therapeutically effective amount of a adenosine reuptake inhibitor, and a therapeutically effective amount of an irreversible proton pump inhibitor. In an exemplary embodiment, the invention provides a single unit oral dosage form comprising a therapeutically effective amount of an adenosine reuptake inhibitor in combination with a therapeutically effective amount of a reversible proton pump inhibitor. In an exemplary embodiment, the invention provides a single unit oral dosage form comprising a therapeutically effective amount of an adenosine reuptake inhibitor in combination with a therapeutically effective amount of an $H_2$ blocker. In an exemplary embodiment, the invention provides a single unit oral dosage form comprising a therapeutically effective amount of an adenosine reuptake inhibitor in combination with a therapeutically effective amount of an alkalizing agent. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

I. c8) Specific Combinations of Dipyridamole with Acid Inhibitors

In an exemplary embodiment, the invention provides a single unit oral dosage form comprising a therapeutically effective amount of dipyridamole in combination with a therapeutically effective amount of an irreversible proton pump inhibitor. In an exemplary embodiment, the invention provides a single unit oral dosage form comprising a therapeutically effective amount of dipyridamole in combination with a therapeutically effective amount of a reversible proton pump inhibitor. In an exemplary embodiment, the invention provides a single unit oral dosage form comprising a therapeutically effective amount of dipyridamole in combination with a therapeutically effective amount of an $H_2$ blocker. In an exemplary embodiment, the invention provides a single unit oral dosage form comprising a therapeutically effective amount of dipyridamole in combination with a therapeutically effective amount of an alkalizing agent. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

I. c9) Specific Combinations of Dipyridamole with Specific Acid Inhibitors

In an exemplary embodiment, the invention provides a single unit oral dosage form comprising a therapeutically effective amount of dipyridamole in combination with a therapeutically effective amount of a PPI selected from omeprazole, esomeprazole, lansoprazole, leminoprazole, rabeprazole, pantoprazole, hydroxyomeprazole, pariprazole, dontoprazole, habeprazole, periprazole, ransoprazole, and tenatoprazole (benatoprazole) and mixtures thereof. In an exemplary embodiment, the invention provides a single unit oral dosage form comprising a therapeutically effective amount of dipyridamole in combination with a therapeutically effective amount of a PPI selected from omeprazole, esomeprazole, lansoprazole, leminoprazole and mixtures thereof. In an exemplary embodiment, the invention provides a single unit oral dosage form comprising a therapeutically effective amount of dipyridamole in combination with a therapeutically effective amount of a PPI selected from omeprazole, esomeprazole and mixtures thereof. In an exemplary embodiment, the invention provides a single unit oral dosage form comprising a therapeutically effective amount of dipyridamole in combination with a therapeutically effective amount of a member selected from ranitidine, cimetidine, nizatidine, famotidine, roxatidine and mixtures thereof in an exemplary embodiment, the invention provides a single unit oral dosage form comprising a therapeutically effective amount of dipyridamole in combination with a therapeutically effective amount of a member selected from ranitidine, cimetidine and mixtures thereof. In another exemplary embodiment, the single unit oral dosage form described in this paragraph further comprises aspirin. In another exemplary embodiment, the single unit oral dosage form described in this paragraph further comprises a therapeutically effective amount of aspirin. In another exemplary embodiment, the single unit oral dosage form described in this paragraph further comprises a non-aspirin NSAID. In another exemplary embodiment, the single unit oral dosage form described in this paragraph further comprises a therapeutically effective amount of a non-aspirin NSAID.

I. d) Additional Components

Additional components can be included in the oral dosage forms described herein. In an exemplary embodiment, the additional component is a third active ingredient. In another exemplary embodiment, the oral dosage form further comprises a therapeutically effective amount of a third active ingredient. In another exemplary embodiment, the oral dosage form does not further comprise a therapeutically effective amount of a fourth active ingredient. In an exemplary embodiment, the additional component is a pharmaceutically acceptable excipient.

I. d1) Aspirin or Non-Aspirin NSAIDs

In some embodiments, the oral dosage form comprises an antiplatelet agent, an acid inhibitor and aspirin. Aspirin or acetylsalicylic acid (acetosal) is a drug in the family of salicylates, often used as an analgesic (against minor pains and aches), antipyretic (against fever), and anti-inflammatory. It has also an antiplatelet ("blood-thinning") effect and is used in long-term low-doses to prevent heart attacks and cancer. The aspirin described for some of the oral dosage forms described herein may or may not be enterically coated.

In other embodiments, the dosage form comprises an antiplatelet agent, an acid inhibitor, and non-aspirin NSAID. Suitable compounds having NSAID activity include, but are non-limited to, the nonselective COX inhibitors, selective COX-2 inhibitors, selective COX-1 inhibitors, and COX-LOX inhibitors, as well as pharmaceutically acceptable salts, isomers, enantiomers, solvates, hydrates, polymorphic crystal forms including the amorphous form, co-crystals, derivatives, prodrugs thereof.

Exemplary non-aspirin NSAIDs include, but are not limited to, celecoxib (Celebrex™); rofecoxib (Vioxx™), etoricoxib (Arcoxia™) meloxicam (Mobic™), valdecoxib, diclofenac (Voltaren™, Cataflam™) etodolac (Lodine™), sulindac (Clinori™), alclofenac, fenclofenac, diflunisal (Dolobid™), benorylate, fosfosal, ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene™), indomethacin (Indocin™), nabumetone (Relafen™), naproxen (Naprosyn™), tolmetin, lumiracoxib, parecoxib, licofelone (ML3000), including pharmaceutically acceptable salts, isomers, enantiomers, derivatives, prodrugs, crystal polymorphs, amorphous modifications, co-crystals, solvates, hydrates, and combinations thereof. The non-aspirin NSAID described for some of the oral dosage forms described herein may or may not be enterically coated.

In one embodiment, the dosage form excludes a non-aspirin NSAID. In another embodiment, it excludes aspirin. In yet another embodiment, it excludes a therapeutically effective amount of a third active agent.

I. d2) Excipients

The oral dosage forms described herein can be prepared by conventional techniques using pharmaceutically acceptable excipients that include, among others, binding agents, fillers, lubricants, disintegrants, emulsifiers, wetting agents, buffers, plasticizers, diluents, coatings, e.g. enteric coatings, pigments or coloring agents, flow agents, glidants, subcoating materials. Common binding agents include, among others, starch, pregelatinized starch, polyvinylpyrrolidone, methylcellulose, hydroxypropylcellulose, hydroxypropylmethylcellulose and PVP (e.g. Povidone K 29-32). Fillers include, among others, lactose, microcrystalline cellulose, mannitol and calcium hydrogen phosphate. Lubricants include, among others, polyethylene glycol (for example PEG 6000), castor oil, hydrogenated castor oil, magnesium stearate, sodium stearyl fumarate, stearic acid and talc. Disintegrants for controlling dissolution and dispersion of the oral formulation include, among others, modified starch, sodium starch glycolate, crospovidone or croscarmellose sodium. Emulsifying and wetting agents include various surfactants both ionic and nonionic and natural or synthetic origin, for example, phospholipids, polysorbates, lecithin, oxypropylene polymers, polyethylene glycols, tweens, pluronics and sodium lauryl sulfate. By way of example, pharma grade sugar can be used in the core for omeprazole pellets or granules; dibasic sodium phosphate as a buffer and diluent; calcium carbonate as an alkaline material and dusting agents or powder for subcoating; sodium lauryl sulfate as a surfactant; hypromellose as a binder or coating; methacrylic acid copolymer as an enteric coating; diethyl phthalate as a plasticizer; talc as a lubricant/glidant; titanium dioxide as a pigment or coloring agent; starch as a disintegrant or core; and colloidal silica as a flow agent or glidant In addition to the actives and acceptable excipients described above, various additives may be included in the oral dosage forms of the invention. These include, but are not limited to, pharmaceutically acceptable flavoring agents, sweeteners, stabilizing agents, preservatives, anti-microbial agents, flow aids, coloring agents, antioxidants, wetting agents, surfactants, emulsifiers, efflux inhibitors and other excipients know to one skilled in the art.

Sweetening or flavoring agents, when present, are preferably in an amount of from about 0.1 to about 80% by weight based on the total weight of the oral dosage form. Suitable sweetening or flavoring agents are well known in the art. Exemplary sweetening agents include, but are not limited to, dextrose, polydextrose, mannitol, saccharine, sorbitol, sucrose, aspartame, acesulfame K, or xylitol.

The oral dosage forms optionally contain pharmaceutically acceptable coloring agents, water-soluble dyes or pigments. Typical coloring agents include, among others, synthetic iron oxides, e.g., FD&C Red, and FD&C Blue. The oral dosage firms optionally contain pharmaceutically acceptable opacifiers, including but not limited to talc.

I. d3) Oral Dosage Forms

A variety of oral dosage forms are disclosed herein and will be apparent to the skilled artisan. Representative formulation technology is taught in, inter alia, Remington: The Science and Practice of Pharmacy, $21^{st}$ Ed., Mack Publishing Co., Easton, Pa. (2006) and Handbook of Pharmaceutical Excipients, $3^{rd}$ Ed, Kibbe, A. H. ed., Washington D.C., American Pharmaceutical Association (2000) each of which are hereby incorporated by reference in their entirety, or in Pharmaceutical Dosage Forms—Tablets, Lieberman, Herbert A., Lachman, Leon, et al., eds., Marcel Decker Inc. (1998). Exemplary oral dosage forms of the present invention can include solids, tablets, capsules, powders, granules, solutions, suspensions, films and other formulations known in the art. Each of the oral dosage forms can optionally comprise an enteric coating. The oral dosage forms can be provided in a single unit or in multiple units. The oral dosage forms may be provided in packets, bottles, blisters, sachets, and other types of containers, and where appropriate, accompanied by a desiccant to provide moisture protection. The oral dosage form may also be provided in a device for providing a measured dose.

In some embodiments, the oral dosage form is a tablet comprising in combination an antiplatelet agent and an acid inhibitor.

In a specific embodiment, the oral dosage form comprises between about 1 mg and 1000 mg of an antiplatelet agent. In another exemplary embodiment, the oral dosage form comprises about 5 mg to 100 mg of antiplatelet agent. In another exemplary embodiment, the oral dosage form comprises about 50-100 mg clopidogrel or about 1-20 mg of prasugrel. In another exemplary embodiment, the oral dosage form is a capsule or a tablet.

The dosage of PPI, e.g. omeprazole, is determined by a careful balance of a sufficient level to provide its beneficial effects on reducing the adverse side effects of the antiplatelet agent, while minimizing its potential effect on reducing the efficacy of the antiplatelet agent. For example, clopidogrel is known to have reduced solubility, which may reduce bioavailability and/or efficacy, at a pH greater than about 4. It has been discovered, at the dosage levels of omeprazole set forth herein, e.g. up to 40 mg or more, the action of omeprazole does not raise the pH level within the upper GI tract to a sufficient extent to substantially reduce clopidogrel bioavailability and thus efficacy. It has been found that a PPI (omeprazole) dose in excess of 10 mg, e.g. up to 40 mg or more, preferably between 15 and 40 mg, more preferably between 20 and 30-40 mg provide the beneficial effects of reducing the adverse side effects of the antiplatelet agent without substantial adverse effects on its efficacy. Moreover, both omeprazole or other proton pump inhibitors and clopidogrel or prasugrel are metabolized by hepatic cytochrome P450, and this metabolism of clopidogrel or prasugrel is necessary for the formation of the active metabolite with its inhibitory effects on ADP-induced platelet aggregation. Coadministration of high doses of omeprazole with clopidogrel can interfere with this metabolism, and hence the efficacy of clopidogrel or prasugrel. The selection of a dose of omeprazole to prevent or reduce gastrointestinal side effects of use of antiplatelet inhibitors must consider these factors to avoid undermining the efficacy.

In a specific embodiment, the oral dosage form comprises between about 1 mg and 1000 mg of acid inhibitor. In another exemplary embodiment, the oral dosage form comprises about 5 mg to 150 mg, 10 mg to 80 mg, 15 mg to 60 mg, or 20 mg to 40 mg of acid inhibitor. In another exemplary embodiment, the oral dosage form comprises at least about 10 to about 80 mg, preferably from about 10 to about 40 mg or more, preferably at least about 10, 15, 20, 25, 30, 35, 40, 45, 50, 55, or 60 mg. A preferred range is from 10 to 40 mg or more preferably from 15 to 35 or 40; or 20 to 30 mg. Useful dosages of omeprazole, esomeprazole or lansoprazole are 10, 15, 20, 25 30, 35, or 40 mg, or amounts therebetween. In another exemplary embodiment, the oral dosage form comprises about 15-30 mg of omeprazole, esomeprazole or lansoprazole. In another exemplary embodiment, the oral dosage form is a capsule or a tablet.

In a specific embodiment, the oral dosage form is a single unit oral dosage form which comprises between about 1 mg and 500 mg of antiplatelet agent and about 1 mg to 500 mg of acid inhibitor. In another exemplary embodiment, the single unit oral dosage form comprises about 5 mg to 100 mg of antiplatelet agent and about 5 mg to 150 mg of acid inhibitor. In another exemplary embodiment, the single unit oral dosage form comprises about 50-100 mg clopidogrel or about 1-20 mg of prasugrel, and the foregoing amounts of omeprazole, esomeprazole or lansoprazole. In another exemplary embodiment, the single unit oral dosage form is a capsule or a tablet.

In a specific embodiment, the tablet comprises about 10-80 mg, preferably about 15-40 mg, of omeprazole and about 50-100 mg clopidogrel or about 1-20 mg of prasugrel granulated with excipients including but not limited to microcrystalline cellulose, mannitol, hydroxypropyl cellulose, lubricant and disintegrating agent.

In a specific embodiment, the tablet comprises about 50-100 mg clopidogrel or about 1-20 mg of prasugrel and an $H_2$ blocker such as about 10-20 mg famotidine or from 50-200 mg ranitidine granulated with excipients which include but not limited to microcrystalline cellulose, lactose, mannitol, disintegrating agents such as croscarmellose sodium or sodium starch glycolate, lubricants such as magnesium stearate, flow aids such as colloidal silica.

Combination pharmaceutical compositions comprising acid inhibitors and other actives, such as NSAIDs are known in the art see for example, U.S. Pat. Nos. 6,926,907; 6,599, 529; 6,365,184; 6,869,615; 6,184,220; 6,284,269, 6,682, 747; 6,613,354 and 6,740,340. The actives and excipients can be compressed into a tablet. In some embodiments, the tablet can comprise one or more enteric coatings and/or enteric coated actives. A variety of tablet formulations with oral dosage forms, combination pharmaceuticals and/or enteric coatings are known in the art, see for example U.S. Pat. Nos. 6,613,354 and 6,740,340.

Granules

In some embodiments, one or more of the active ingredients in the oral dosage forms described herein are located on and/or embedded within granules, pellets, or beads. These granules can contain a selected percentage of one or more active ingredients, with the remainder of its mass consisting of inactive ingredients. Examples of these inactive ingredients include, but are not limited to, sugar, calcium carbonate, sodium bicarbonate, sodium phosphate dibasic, methacrylic acid copolymer, cellulose acid phthalate, hydroxymethylpropylcellulose phthalate, hydroxypropylcellulose and hypromellose.

The percentage of the weight of the active ingredient which constitutes the weight of the granule is known as the drug loading level. The drug loading level for an active ingredient in an oral dosage form is an average. Some of the granules may contain little or no active ingredient, while others may contain greater amounts than the percentage stated. To the extent that a physically smaller oral dosage form is desired, the drug loading level will need to be increased. Higher drug loading levels allow the physical size of the oral dosage form to be decreased.

In another exemplary embodiment, the acid inhibitor is a proton pump inhibitor, and the proton pump inhibitor is present in and/or on granules. In yet another exemplary embodiment, the acid inhibitor is a proton pump inhibitor, and the proton pump inhibitor is present in and/or on granules, and the granules have an enteric coat. In an exemplary embodiment, the drug loading level of an active ingredient in and/or on a granule in an oral dosage form described herein is from about 1% to about 50%. In another exemplary embodiment, the active ingredient is an acid inhibitor, and its drug loading level is from about 5% to about 25%. In yet another exemplary embodiment, the drug loading level of the acid inhibitor is from about 6% to about 15%. In yet another exemplary embodiment, the drug loading level of the acid inhibitor is from about 7% to about 13%. In yet another exemplary embodiment, the drug loading level of the acid inhibitor is from about 8% to about 12%. In yet another exemplary embodiment, the acid inhibitor is a proton pump inhibitor, and the proton pump inhibitor is present in and/or on granules, and the weight of the proton pump inhibitor in and/or on the granule is from about 7 percent to about 13 percent of the total weight of the granule.

Enteric Coatings

In some embodiments, one or more active ingredients in the oral dosage forms described herein are enterically coated. In other embodiments, one or more units of the oral dosage forms described herein are enterically coated. In another exemplary embodiment, essentially all of said proton pump inhibitor is enterically coated. As is well known in the art, some active agents, such as proton pump inhibitors are acid sensitive or labile, susceptible to degradation and/or transformation in acidic media. The degradation of proton pump inhibitors and can be stabilized in mixtures with alkaline compounds. The stability of this class of antisecretory compounds is also affected by moisture, heat, organic solvents and, to some degree, by light. With respect to the stability properties of the proton pump inhibitors, it is preferable that, in an oral solid dosage form, they be protected from contact with the acidic gastric juice. The active substance is preferably transferred in intact form to that part of the gastrointestinal tract where pH is near neutral and where rapid absorption of the medication can occur. Formulations which address the degradation of proton pump inhibitors in acidic media are described in U.S. Pat. Nos. 4,786,505; 5,817,338; 5,798,120; and 6,551,621 for example, and each of the described formulations in those patents can be modified to include one or more antiplatelet agents pursuant to the present invention. Generally, the enteric material is insoluble in acid environments, such as the stomach, but is soluble in near-neutral environments such as the small intestine. Because of the enteric properties, the coated material can pass through the stomach essentially undissolved and the actives can be released in the lower part of the intestinal tract. In some embodiments, the enteric coating dissolves at a pH of between 5 and 7.5.

In some embodiments, the oral dosage form comprises granules that are enterically coated prior to being incorporated into the oral dosage form. In some embodiments, the granules contain acid inhibitors such as PPIs, e.g., omeprazole. In some embodiments, the acid inhibitor is enterically coated and the antiplatelet agent is not enterically coated. In other embodiments, the antiplatelet agent is enterically coated and the acid inhibitor is not enterically coated. In other embodiments, an enteric coat covers both the acid inhibitor and the antiplatelet agent, and any other components of the oral dosage form. In other embodiments, a first enteric coat covers the acid inhibitor and a second enteric coat covers the antiplatelet agent. In some embodiments, the antiplatelet agent is in the form of enteric coated multiparticulate units and the acid inhibitor is in the form of granules or alternatively in the form of modified release formulated units such as enteric coating layered units or units layered with a controlled release layer. In another embodiment, the acid inhibitor is in the form of enteric coated multiparticulate units and the antiplatelet agent in the form of granules or alternatively in the form of modified release formulated units such as enteric coating layered units or units layered with a controlled release layer. Examples of multiparticulate units are pellets, granules, or beads.

Various enteric materials are known in the art, a number of which are commercially available. Exemplary enteric coatings of use in the present invention can be any enteric material known to those skilled in the art, see for example, U.S. Pat. Nos. 6,855,702 and 6,605,300. The enteric materials usually comprises a polymer with enteric properties. Suitable non-limiting examples include methacrylic acid copolymers such as methacrylic acid/methyl methacrylate copolymers, methacrylic acid/ethyl acrylate copolymers, methacrylic acid/methyl acrylate/methyl methacrylate copolymers, shellac, hydroxypropyl methylcellulose phthalate, hydroxypropyl methyl cellulose acetate-succinates, hydroxypropylmethylcellulose trimellitate, cellulose acetate-phthalates, polyvinyl acetate phthalate or a mixture of these components, or other suitable enteric materials.

In some embodiments, enteric coating layer(s) are applied using standard coating techniques. The enteric coating is applied using a variety of methods known in the art, such as spraying or layering see for example U.S. Pat. Nos. 4,287,221 and 6,605,300. The thickness of the enteric coating is designed based on the nature of the coating material and the desired lag time or delay in release of the oral dosage form ingredients. The enteric coating(s) may be applied to the outside surface of an oral dosage form, or a coating, using a suitable coating technique. The enteric coating layer material may be dispersed or dissolved in either water or in a suitable organic solvent for coating.

In some embodiments the enteric coating contains an effective amount of a pharmaceutically acceptable plasticizer to obtain the desired mechanical properties, such as flexibility of the enteric coating layers. Such plasticizers are, for example and without limitation, triacetin, citric acid esters, phthalic acid esters, dibutyl sebacate, cetyl alcohol, diethyl phthalate, triethyl citrate, polyethylene glycols, polysorbates or other plasticizers. The amount of plasticizer is optimized for the particular situation. The amount of plasticizer is preferably above 10% by weight of the enteric coating polymer(s), preferably 15-50%, and more preferably 20-50%. Additives such as dispersants, colorants, pigments, anti-tacking agents may also be included into the enteric coating layer(s). Other compounds may be added to increase film thickness or opacity and to decrease diffusion of acidic gastric juices into the dosage form.

As set forth above, PPIs are acid sensitive. In certain embodiments, enteric coating materials such as methacrylic acid copolymers are sufficiently acidic to cause degradation of PPI. To avoid this, a sub-coating or intermediate barrier, e.g., formed of hypromellose and or include a basic buffering or alkaline reagent such as calcium carbonate or sodium phosphate dibasic, such as disclosed in U.S. Pat. No. 4,738,974 may bee used for the PPI.

As will be appreciated by one skilled in the art, overcoating may be applied to the enteric coated oral dosage form, for example, as a protective layer, flavor, and the like. Suitable overcoating materials include, but are not limited to, sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium and the like. Additives such as plasticizers, colorants, pigments, fillers, anti-tacking and anti-static agents, such as for instance magnesium stearate, titanium dioxide, talc and other additives may also be included in the over-coating layer(s).

Several benefits are derived from the enteric coated oral dosage forms provided herein. For example, the enteric coating protects the actives, for example proton pump inhibitors, from acid degradation in the stomach. In addition, manufacturing costs can be significantly reduced and productivity increased because there is no need to enteric coat the individual active agents of the oral dosage form. Also, there is no need to enteric coat individual units of the proton pump inhibitor and formulate the enteric coated proton pump inhibitor with the other ingredients in such a way as to not compromise the integrity of the protective enteric coating. Accordingly, antiplatelet agents or aspirin can be delivered in an enteric coated dosage form with a minimum of gastrointestinal side effects.

Capsules

In an exemplary embodiment, the oral dosage form described herein can be provided as orally administrable capsules, e.g. hard or soft gelatin capsules, or other encapsulated dosage forms such as HPMC capsules, known in the art. The capsule wall can include any of the various materials conventionally used in the pharmaceutical industry, including, by way of example and not limitation, gelatin, carrageenins, polysaccharide (e.g., agar, hydroxypropyl methylcellulose, hydroxyethylcellulose, pectin, starch etc. or mixtures thereof). Suitable hard gelatin capsules are supplied by Capsugel. Suitable HPMC capsules are supplied by Shinogi.

The orally administrable capsule can comprise substrates, suspensions, or an aqueous solution of one or more active agents. For example, hard gelatin capsules can be filled with powders, warm solutions or suspensions of active agents in waxy and/or lipid based formulations that solidify in the capsule when cooled to room temperature. Soft gel capsules can be filled with solutions or suspensions of the antiplatelet agent and the acid inhibitor in oil and/or lipid and/or solvents such as PEG or propylene glycol.

The antiplatelet agent and the acid inhibitor can be dry mixed and filled into a capsule. The capsule can include a plasticizer, such as glycerin, triacetin, sorbitol, polyethylene glycol, propylene glycol, citrate, and phthalate, to impart form and flexibility where desired.

In some embodiments, the orally administrable capsule includes an enteric coating. In some embodiments, the active, or active containing substrates, such as granules, are enterically coated prior to being filed in the capsule. In some embodiments, the acid inhibitor is in the form of enteric coated multiparticulate units and the antiplatelet agent in the form of granules or alternatively in the form of modified release formulated units such as enteric coating layered units or units layered with a controlled release layer.

In a specific embodiment, the capsule comprises about 10-80 mg, preferably about 15-30 mg, of omeprazole, esomeprazole or lansoprazole and about 50-100 mg clopidogrel or 1-20 mg of prasugrel wherein the capsule is coated with a film forming polymer including but not limited to acrylic co-polymers or cellulose acetate phthalate and plasticizers.

In a specific embodiment, the capsule comprises about 10-80 mg of omeprazole, esomeprazole or lansoprazole and about 50-100 mg clopidogrel or 1-20 mg of prasugrel in an oil based matrix which includes but is not limited to soybean oil, olive oil, cone oil, or lipid derived excipients such as Gelucires™.

Conventional Tablets

The oral dosage forms described herein may be in the form of a conventional compressed tablet. See, Remington's Pharmaceutical Sciences, Mack Publishing. In an exemplary embodiment, an antiplatelet agent and an acid inhibitor may be intimately mixed with each other and compressed into a conventional tablet.

The tableted dosage form can include an enteric coated acid inhibitor, with an antiplatelet agent constituting the rest of the active ingredients of the compressed tablet. Preferably, the enteric coated acid inhibitor has properties such that the compression of the actives into a tablet does not significantly affect its acid resistance, see for example U.S. Pat. No. 6,613,354. This may require a greater concentration of plasticizer in the coating than would be required for capsules and adroit selection of other tableting excipients for compressibility.

Alternatively, the antiplatelet agent and an acid inhibitor may be intimately mixed with each other and compressed into a conventional tablet and the entire tablet enterically coated, see for example U.S. Pat. No. 6,926,907. In this configuration, the tablet contains the acid inhibitor and antiplatelet agent in the required doses along with appropriate excipients, and optionally agents to aid dissolution, lubricants, fillers, etc. Here, the entire tablet may be enterically coated to protect the PPI.

Multilayer Tablets

Another suitable dosage form is a multilayer tablet, see for example U.S. Pat. Nos. 6,926,907 and 6,132,768. In the multilayer tablet, the first component may be compressed into one layer, with the second component being subsequently added as a second layer of the multilayer tablet. Optionally, one or more subcoats or barrier coats may be added prior to the second layer or prior to adding an enteric coating, see for example U.S. Pat. No. 6,926,907.

In a specific embodiment, the multilayer tablet comprises one portion containing an acid inhibitor, preferably omeprazole, optionally combined with appropriate excipients, agents to aid dissolution, lubricants, fillers, etc. The second portion of the tablet comprises the antiplatelet agent, preferably clopidogrel or prasugrel, optionally combined with other excipients, dissolution agents, lubricants, fillers, etc. In some embodiments, the acid inhibitor can be enterically coated. Alternatively, a layer of the multilayer tablet, or the entire tablet can be enterically coated.

In some embodiments, the multilayer tablet comprises the antiplatelet agent in the core of the tablet and the acid inhibitor covers the core. In some embodiments, clopidogrel or prasugrel are in the core of the tablet and the acid inhibitor covers the core. In some embodiments, the acid inhibitor can be enterically coated granules. Alternatively, in some embodiments the multilayer tablet comprises the antiplatelet agent in the core of the tablet and the acid inhibitor covers the core, wherein the entire tablet is enterically coated. For examples of enterically coated tablets see for example U.S. Pat. No. 6,926,907. In some embodiments, clopidogrel or prasugrel are in the core of the tablet, omeprazole covers the core, and the entire tablet is enterically coated.

Alternatively, the multilayer tablet comprises the acid inhibitor in the core of the tablet and the antiplatelet agent covers the core. In some embodiments, clopidogrel or prasugrel covers the core of the tablet. In some embodiments, the multilayer tablet comprises an enterically coated acid inhibitor in the core of the tablet and the antiplatelet agent covers the core. In some embodiments, the enterically coated acid inhibitor is omeprazole. Alternatively, in some embodiments the multilayer tablet comprises the acid inhibitor in the core of the tablet, and enteric coating covering the core, and the antiplatelet agent covers the enteric coating. Alternatively, in some embodiments the multilayer tablet comprises the acid inhibitor in the core of the tablet and the antiplatelet agent covers the core, wherein the entire tablet is enterically coated.

Controlled-Release

In some embodiments, the oral dosage forms described herein provide controlled release of one or more actives using one or more controlled release agents. A variety of controlled release pharmaceutical compositions are known in the art, see for example U.S. Pat. Nos. 6,861,072; 6,599,539 and 6,905,708. The term "controlled release" is intended to mean the release of actives at a pre-selected or desired rate. This rate will vary depending upon the application. Desirable rates include fast or immediate release profiles as well as delayed, sustained or sequential release. Combinations of release patterns, such as initial release followed by lower levels of sustained release of active are specifically contemplated.

Further alternatives are exemplified wherein the acid inhibitor is enterically coated and the antiplatelet agent is in contained in a polymeric swelling or eroding matrix, such as a polymeric matrix resulting in a preparation providing extended release of the antiplatelet agent, see for example U.S. Pat. No. 6,413,354. In an exemplary embodiment, the antiplatelet agent in the gelling matrix is clopidogrel or prasugrel. In another exemplary embodiment, the antiplatelet agent in the gelling matrix clopidogrel or prasugrel and the acid inhibitor is omeprazole, esomeprazole or lansoprazole.

Effervescents

The active agents may further be included in an effervescent dosage form, see for example U.S. Pat. No. 6,964,978. One or more effervescent agents can be used as disintegrants and/or to enhance organoleptic properties of compositions of the invention. When present in compositions of the invention to promote dosage form disintegration, one or more effervescent agents are preferably present in a total amount of about 30% to about 75%, and preferably about 45% to about 70%, for example about 60%, by weight of the composition.

In some embodiments, an effervescent agent, present in a dosage form in an amount less than that effective to promote disintegration of the dosage form, provides improved dispersion of the actives in an aqueous medium. Without being bound by theory, the effervescent agent can be effective to accelerate dispersion of actives from the dosage form in the gastrointestinal tract, thereby further enhancing absorption and rapid onset of therapeutic effect. When present in a dosage form of the invention to promote intragastrointestinal dispersion but not to enhance disintegration, an effervescent agent is preferably present in an amount of about 1% to about 20%, more preferably about 2.5% to about 15%, and still more preferably about 5% to about 10%, by weight of the composition.

An effervescent agent is an agent comprising one or more compounds which, acting together or individually, evolve a gas on contact with water. The gas evolved is generally oxygen or carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid.

Non-limiting examples of suitable bases as components of effervescent agents useful in the invention include carbonate salts (e.g., calcium carbonate), bicarbonate salts (e.g., sodium bicarbonate), sesquicarbonate salts, and mixtures thereof.

Non-limiting examples of suitable acids as components of effervescent agents useful in the invention include citric acid, tartaric acid, malic acid, fumaric acid, adipic acid, succinic acid, acid anhydrides of such acids, acid salts of such acids, and mixtures thereof.

In a specific embodiment, the effervescent dosage comprises about 50-100 mg clopidogrel or about 1-20 mg of prasugrel and about 10-80 mg, preferably about 15-40 mg, of enteric coated omeprazole, esomeprazole or lansoprazole granules. Effervescent components include but are not limited to sodium bicarbonate and citric acid. Other components of the tablets include but are not limited to microcrystalline cellulose, lactose, mannitol, croscarmellose sodium and magnesium stearate.

Orally Administrable Tablets

Orally administrable tablets can be used, either as a single unit or multiunit oral dosage form or as part of a multiunit oral dosage form. In an exemplary embodiment, the single unit orally administrable tablet can comprise an antiplatelet agent, and an acid inhibitor see for example U.S. Pat. Nos. 6,723,348; 6,692,771; 6,365,182; 6,221,392; 6,899,899; and 7,008,640. In some embodiments, the orally administrable tablet comprises antiplatelet agent, an acid inhibitor and a gel-forming water-soluble polymer. Additional pharmaceutically acceptable excipients include, but are not limited to, a surfactant, agents, such as sodium bicarbonate, to improve the dissolution or absorption of the actives. In a specific embodiment, the orally administrable tablet comprises about 50-100 mg clopidogrel or about 1-20 mg of prasugrel and about 10-80 mg, preferably about 15-30 mg, enteric coated omeprazole granules.

Chewable Tablets

In an exemplary embodiment, the oral dosage form described herein can be in a chewable tablet. Chewable tablets usually contain large amounts of pleasant-tasting substances such as mannitol in the formulation, and are known in the art, see for example U.S. Pat. Nos. 7,014,862 and 7,008,640. In a specific embodiment, the chewable tablet comprises about 50-100 mg clopidogrel or about 1-20 mg of prasugrel and about 10-80 mg, preferably about 15-30 mg, of an acid inhibitor.

Orally Administrable Films

In an exemplary embodiment the oral dosage form described herein can be in the form of an orally administrable film. It is specifically contemplated that the amount of active agents in the film is dependent on the type of film, thickness and surface area of film.

It is contemplated that the orally administrable films described herein can comprise a single film layer or multiple film layers. For example, it may be desirable to form an orally administrable film comprising a first active and a second film comprising a second active which may be layered onto the first film. One or more of the films may impart modified release characteristics to the formulation.

In some embodiments, the orally administrable films comprise an antiplatelet agent and a proton pump inhibitor. In other embodiments, the orally administrable films comprise an antiplatelet agent and a $H_2$ blocker. In still other embodiments, the orally administrable films comprise an antiplatelet agent and reversible proton pump inhibitor.

Orally administrable films and methods for making such films are well known in the art. See for example: U.S. Pat. Nos. 4,136,145; 4,713,243; 5,166,233; 5,700,478; 5,800,832, 5,948,430; 6,419,903, 6,177,096; 6,284,264; 6,596,298; 6,656,493; 6,709,671; 6,824,829; 6,923,981, and United States Patent Application Publication Nos.: US 2001/0046511; US 2001/0022964; US 2002/0131990; US 2003/0107149; US 2004/0151756, US 2004/0241242; US 2004/0247649; US 2004/0258896; US 2005/0184427; US 2005/0196358; US 2005/0075432 and US 2005/0037055.

The orally administrable film can be prepared as described in U.S. Pat. No. 6,709,671, for example, Polyalcohol, surfactants, plasticizers, and possible other ingredients except the water-soluble or water-dispersible polymers are dissolved in a sufficient amount of a solvent which is compatible with them. Examples of compatible solvents include water, alcohols or mixtures thereof. After a clear solution is formed, the water-dispersible polymer or mixture of water-dispersible polymers is slowly added with stirring, and heating if necessary, until a clear and homogeneous solution is formed, followed by the addition of actives and flavors. The solution is coated onto a suitable carrier material and dried to form a film.

In some embodiments, the orally administrable film can be prepared as described in U.S. Patent Appl. No. 2005/0184427. Briefly the desired components are combined to form a multi-component matrix, including the polymer, water, and an active or other components as desired, and the combination is formed into a sheet or film, by any method known in the art such as extrusion, coating, spreading, casting or drawing the multi-component matrix. If a multi-layered film is desired, this may be formed by co-extruding more than one combination of components which may be of the same or different composition. A multi-layered film may also be formed by coating, spreading, or casting a combination of components onto an already formed film layer.

As described above, the desired actives can be mixed with the film forming solution to form the desired orally administrable film. The actives can be uniformly dispersed in the film forming solution in the form of insoluble solid particles together and/or as soluble actives. In some embodiments antiplatelet agent and enteric coated proton pump inhibitor granules are added to the film forming solution. In other embodiments clopidogrel or prasugrel powder and enteric coated omeprazole, esomeprazole or lansoprazole granules are added to the film forming solution.

In some embodiments, antiplatelet agent may be added to the film forming polymer solution in the form of granules together with the enteric coated proton pump inhibitor granules. In some embodiments, clopidogrel or prasugrel may be added to the film forming polymer solution in the form of granules together with the enteric coated omeprazole, esomeprazole or lansoprazole granules.

In some embodiments, the antiplatelet and/or acid inhibitor may be incorporated into the film-forming mixture in liquid form, such as in solution or suspension rather than as film coated solid particles. This is particularly useful for acid inhibitors, such as reversible proton pump inhibitors, that do not require an enteric coat.

The orally administrable films generally comprise one or more polymers as well as fillers as desired. Film-forming polymers are well known in the art. See for example, U.S. patent application Ser. No. 11/092,217. Generally, the polymer can be water soluble, water insoluble, water swellable or a combination thereof. In some embodiments the polymer can include cellulose or a cellulose derivative. Suitable non-limiting examples of water soluble polymers include carboxymethyl cellulose hydroxypropylmethyl cellulose, hydroxyethyl cellulose, hydroxypropyl cellulose, polyvinyl pyrrolidone, polyvinyl alcohol, pullulansodium aginate, polyethylene glycol, acacia gum, arabic gum, xanthan gum, tragancanth gum, guar gum, polyacrylic acid, methylmethacrylate copolymer, carboxyvinyl copolymers, starch, and combinations thereof. Suitable non-limiting examples of water insoluble polymers include cellulose acetate, hydroxypropyl ethyl cellulose, hydroxypropyl methyl cellulose, phthalateethyl cellulose, phthalate and combinations thereof.

Also provided herein are orally administrable films with one or more enteric coated pharmaceutical agents. Enteric coated pharmaceutical agents and methods for making such agents are well known in the art; see for example the following references, each of which is hereby incorporated by reference in its entirety: U.S. Pat. Nos. 4,786,505; 6,013,281; 6,365,184; 6,296,876; 6,780,435; and 6,926,907. In some embodiments, the orally administrable film comprises an antiplatelet agent and an acid inhibitor. In an exemplary embodiment, the acid inhibitor is enteric coated. In some embodiments, the acid inhibitor can be coated onto the surface of a substrate and overcoated with an enteric coating.

The concentration of enteric coated actives in the orally administrable films should be suitable for therapeutic benefit without causing adverse feeling, such as grittiness, in the mouth. The amount of enteric coated actives in the orally administrable films depends on the kind of active and is usually between about 0.01 and about 20% to as high as 30% (w/w), and it can be higher if necessary to achieve the desired effect.

In some embodiments, the orally administrable film comprises an antiplatelet agent and an acid inhibitor, wherein one or more of the actives are coated onto the surface of a particulate substrate. In some embodiments, the orally administrable film comprises an antiplatelet agent and an acid inhibitor, wherein one or more of the actives is coated onto the surface of a particulate substrate and the acid inhibitor is not enteric coated. This embodiment can be used for an acid inhibitor that does not require an enteric coating, e.g. a reversible proton pump inhibitor or H, blocker. In a specific embodiment, the orally administrable film comprises an antiplatelet agent and a reversible proton pump inhibitor, wherein the reversible proton pump inhibitor is coated onto the surface of particulate substrates and the reversible proton pump inhibitor is not enteric coated.

In another embodiment, the orally administrable films comprise a combination of an antiplatelet and an acid inhibitor, in which the acid inhibitor is enteric coated. Suitable non-limiting examples of proton pump inhibitors, that can be enteric coated, include omeprazole (Prilosec™), esomeprazole (Nexium™), lansoprazole (Prevacid™), leminoprazole, rabeprazole (Aciphex™), and pantoprazolem (Protonix™), as well as pharmaceutically acceptable salts, polymorphic crystal forms, isomers, amorphous modifications, co-crystals, derivatives, prodrugs, enantiomers, and combinations thereof.

In a specific embodiment, the orally administrable film comprises clopidogrel or prasugrel and enteric coated omeprazole, esomeprazole or lansoprazole.

In some embodiments, orally administrable films provide controlled release of one or more actives using one or more controlled release agents. The polymers in orally administrable films may also be chosen to be the agents for controlled release of one or more pharmaceutical ingredients. In some embodiments, controlled release can be achieved by providing a substantially water insoluble film that incorporates one or more pharmaceutical ingredients that will be released from the film over time. In some embodiments, a variety of different water soluble or insoluble polymers can be used and optionally include biodegradable polymers in combination.

In some embodiments, one or more active ingredients employed in the present invention can be incorporated into the film in a controlled release form. For example, active ingredients can be coated with polymers such as ethyl cellulose or polymethacrylate.

Additional components can be incorporated into the films of the present invention include, without limitation, colorants, flavors, fragrances, mouthwash components, preservatives, sweetening agents, vitamins, antioxidants and combinations thereof. Additional components can include, without limitation, surfactants and plasticizers for compartmentalizing the components within the mixture; polyalcohols; and thermo-setting gels such as pectin, carageenins, and gelatin, which can help maintain the dispersion of components. Citric acid, or other suitable agent, can be added to stimulate saliva production and facilitate rapid dissolution of the film in the oral cavity, and/or provide an acidic environment for an enteric coated proton pump inhibitor.

In some embodiments, the dissolving film can be adhered to the oral cavity thereby releasing the active ingredients of the oral dosage form, for example antiplatelet agent and acid inhibitor. In some embodiments, the dissolving film can be adhered to the oral cavity thereby releasing some of the active ingredients locally in the oral cavity. For example, the invention provides a dissolving film comprising an antiplatelet agent and an enteric coated proton pump inhibitor, in which the antiplatelet agent is released into the oral cavity, while the enteric coated proton pump inhibitor remains insoluble in the oral cavity and swallowed intact.

Optionally, the orally administrable film formulation may contain a combination of plasticizers, surfactants, colorants, sweetening agents, flavors, flavor enhancers, and/or other excipients commonly used to modify the taste of formulations intended for application to the oral cavity.

The orally administrable films provided herein can accommodate a wide range of amounts of the active ingredients. As understood by one skilled in the art, the amount of actives incorporated into the film depend in part on the type of film, polymer, surface area, and thickness of the film. In some embodiments, the amount of actives to film is between about 0.01 and about 50% (w/w), but it can be higher if necessary to achieve the desired effect.

Active Ingredients in Separate Units

In some embodiments, the invention comprises a package comprising a unit of therapeutically effective amount of an antiplatelet agent, and a separate unit of a therapeutically effective amount of an acid inhibitor. In some embodiments, the oral dosage form can be provided in packaging in which one or more antiplatelet agents and an acid inhibitor are provided in separate units in the same oral dosage form or package or container, for co-administration. Suitably, the units for each of the antiplatelet agent and acid inhibitor can be tablets, capsules, films, powders, granules, solutions, solids, suspensions and or other acceptable oral dosage forms. For example, one of the units can contain the antiplatelet agent but not the acid inhibitor and another of the units in the packaging can contain the acid inhibitor but not the antiplatelet agent. In a specific example, a tablet of clopidogrel bisulfate or prasugrel and a capsule of enteric coated omeprazole, esomeprazole or lansoprazole granules can be placed in the same blister pack for co-administration. These combinations may be provided, for example, in packaging, such as kits, blister packs, packets or bottles shrink-wrapped together in which more than one dosage form of the various components are provided in the same dispensing unit for co-administration.

In some embodiments a kit is provided in which one or more sheets of blister packs comprising a dosage form of one or more antiplatelet agents and one or more sheets of blister packs comprising dosage forms of an acid inhibitor. In some embodiments, the kit comprises a plurality of sheets of blister packs, wherein each sheet comprises at least one blister pack comprising the dosage form of one or more antiplatelet agents and at least one blister pack comprising the dosage form of an acid inhibitor. The dosage form for each of the antiplatelet agents and acid inhibitors is selected from the group consisting of tablets, capsules, films, powders, granules, solutions, solids, suspensions and another acceptable oral dosage forms.

The oral dosage forms can be packaged in sealed, air and moisture resistant packages to protect the actives from exposure to the environment and from oxidation, hydrolysis, volatilization resulting from interaction with the environment. The packaged oral dosage forms can contain a fill supply of the medication typically prescribed for the intended therapy. A series of unit doses can be packaged together in accordance with the prescribed regimen or treatment, e.g., a 3-90 day supply, depending on the particular therapy.

A number of benefits are derived from the oral dosage forms provided herein. For example, the orally administrable tablets, chewable tablets and oral film strip formulations can be administered without water. These methods of drug administration, without the need for water, are also particularly well suited for a mobile society. The oral dosage forms provided herein can be particularly appealing to subjects with difficulty in swallowing pharmaceuticals, such as children, elderly, and also in veterinary practice. For example, dosage forms, including tablets and films, placed in the sublingual area are suitable for non-enteric coated acid inhibitors as absorption from a sublingual dosage form is generally fast and avoids first pass metabolism.

In addition, the oral dosage forms provided herein provide for accurate dosage amounts. For example, in the oral film strip formulations the dosage amount can be determined by the size of the film and concentration of the active in the original polymer/water or polymer/solvent combination.

Daily Usage of Oral Dosage Forms

The oral dosage forms described herein can comprise an antiplatelet agent and an acid inhibitor in therapeutically effective amounts. As with other pharmaceuticals, it will be understood that the total daily usage of a pharmaceutical composition of the invention will be decided by a patient's physician. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and other factors known to those of ordinary skill in the medical arts. For example, it is well within the skill of the art to start doses of the compound at levels lower than required to achieve the desired therapeutic effect and to gradually increase the dosage until the desired effect is achieved.

The skilled artisan can adjust the amount of active ingredient in the oral dosage forms or administered to a patient based upon standard techniques well known in the art. The dosage form can be administered at a dosage level up to and above conventional dosage levels for antiplatelet agents and acid inhibitors. General guidelines for dosing antiplatelet agents and acid inhibitors are known in the art.

Suitable dosage levels will depend in part upon the effectiveness of the chosen actives and conditions to be treated. Generally, the daily therapeutically effective amount of the actives administered to a subject in doses typically range from about 0.1 to about 100 mg/kg body weight. The oral dosage form can be administered once, twice, three, of four or more times daily in order to achieve the daily therapeutically effective amount of the actives.

Incorporating two or more actives, and optionally additional active ingredients and/or pharmaceutically acceptable excipients, in a single unit oral dosage form would improve patient compliance. For example, when patients have to take multiple drugs once or several tunes a day, patient compliance suffers and leads to therapeutic failure. The improvement in patient compliance could be more significant in cases in which drugs must be administered several times every day.

In some embodiments, each dosage form will comprise about 0.1-200 mg of the acid inhibitor and about 0.1-1,000 mg of the antiplatelet agent. Preferably, each dosage form will comprise about 10-80 mg of the acid inhibitor and about 5-500 mg of the antiplatelet agents, and more preferably about 10-40 mg acid inhibitor and about 50-100 mg of the antiplatelet agent, respectively.

In a specific embodiments, the oral dosage form comprises clopidogrel. In some embodiments, the dosage form will comprise about 20-200 mg clopidogrel. Preferably, the dosage form will comprise about 40-100 mg of clopidogrel, and more preferably about 25, 50, or 75 mg clopidogrel.

In a specific embodiments, the oral dosage form comprises prasugrel. In some embodiments, the dosage form will comprise about 1-20 mg prasugrel. Preferably, the dosage form will comprise about 4-11 mg of prasugrel, and more preferably about 5 or 10 mg of prasugrel.

In some embodiments, the oral dosage form comprises omeprazole. In some embodiments, the dosage form will comprise about 10-100 mg omeprazole. Preferably, the dosage form will comprise about 10-80 mg, preferably about 15-30 mg, of omeprazole, and more preferably about 10, 20, 30, 40, or 50 mg omeprazole. Suitable preferred dosages of certain potential active ingredients include esomeprazole (about 20 to about 40 mg), sulfinpyrazone (about 100 to about 200 mg), or famotidine (about 10, about 20, or about 40 mg), etc.

II. Methods of Use

Provided herein are methods of inhibiting platelet aggregation and/or treating, reducing and/or preventing a gastrointestinal disorder in a subject comprising orally administering, either as a single unit or as multiple units in a single package, a therapeutically effective amount of one or more antiplatelet agents and one or more acid inhibitors. Also provided herein are methods of inhibiting platelet aggregation and/or treating, reducing and/or preventing a gastrointestinal disorder in a subject comprising orally administering to a subject an oral dosage form described herein. In an exemplary embodiment, the subject is not otherwise in need of treatment for platelet aggregation and/or a gastrointestinal disorder.

Also provided are methods of treating a subject comprising orally administering to a subject, either as a single unit or as multiple units in a single package, one or more antiplatelet agents and one or more acid inhibitors and optionally, one or more additional pharmaceutical agents. The term "co-administration" refers to the administration of one or more antiplatelet agents, one or more acid inhibitors, and optionally one or more additional pharmaceutical agents, at approximately the same time or in close sequence so that their effects run approximately concurrently or substantially overlap. Although no specific time is required, co-administration can be within 60, 30, 15, 10, 5, or 1 minute or less.

Provided herein are methods of inhibiting a gastrointestinal disorder in a subject who is not otherwise in need of such treatment, comprising administering an oral dosage form which includes a therapeutically effective amount of one or more antiplatelet agents and one or more acid inhibitors.

Also provided are methods of treating a subject comprising orally co-administering to a subject one or more antiplatelet agents and one or more acid inhibitors wherein the antiplatelet agent and acid inhibitor are provided in separate units. In some embodiments, the separate units are provided in the same package or container. In embodiments wherein the oral dosage form is provided as one or more antiplatelet agents and one or more acid inhibitors in separate units in the same package or container, the oral dosage form is co-administered to a subject at approximately the same time or in close sequence so that their effects run approximately concurrently or substantially overlap. For example, a subject can co-administer an oral dosage form comprising an antiplatelet agent and an acid inhibitor provided in separate units in the same package, by opening the package and placing the individual units in the oral cavity. In some embodiments, the subject can co-administer an oral dosage form comprising an antiplatelet agent and an acid inhibitor provided in separate units in the same package, by opening the package and placing the individual units in the oral cavity at approximately the same time. In some embodiments, the subject can co-administer an oral dosage comprising an antiplatelet agent and an acid inhibitor provided in separate units in the same package, by opening the package and placing the individual units in the oral cavity within 60, 30, 15, 10, 5, or 1 minute or less.

The methods described herein can comprise administering to a subject one or more antiplatelet agents, one or more acid inhibitors, and one or more additional active ingredients. It is to be understood the method comprises the administration of an antiplatelet agent, acid inhibitor, and additional active ingredients in a single dosage form, as well as the co-administration, and/or administration in combination, of an antiplatelet agent, acid inhibitor, and additional active ingredients in separate units, as part of a multiunit oral dosage form. In some embodiments, the additional active ingredient is aspirin. In another exemplary embodiment, the additional active ingredient is a non-aspirin NSAID. Suitable compounds having NSAID activity are described herein. In a specific embodiment, the method comprises administering to a subject, either as a single unit or as multiple units in a single package, clopidogrel or prasugrel, omeprazole esomeprazole or lansoprazole, and aspirin.

The oral formulations and methods described herein can be used to treat, prevent or reduce the risk of almost any physiological disorder for which antiplatelet agents and/or acid inhibitors are indicated. The methods and formulations provided herein can be administered to any subject in need of therapy including, without limitation, humans, including patients, companion animals, including, but not limited to dogs, cats, ferrets, and birds, food-source animals, including, but not limited to cows, pigs, and sheep, and zoo animals, such as monkeys and other primates, and other similar animal species.

The methods and formulations provided herein can be administered to a subject in need of therapy for disorders for which antiplatelet agents are typically indicated. In general, the formulations provided herein can be used whenever antiplatelet therapy, or inhibition of platelet aggregation, and the like, is needed. For example, the formulations provided herein can be used to treat, prevent or reduce the risk of formation of thrombi and thromboembolic and therefore to treat, prevent or reduce the risk of thrombotic occlusions and reocclusions. The methods and formulations provided herein can be used for preventing or reducing the risk of occurrence of platelet thrombosis, thromboembolism and reocclusion after acute intervention such as atherectomy, angioplasty, coronary artery bypass procedures or cardiac valve replacement. The combination therapy can also be used for preventing or reducing the risk of occurrence of platelet thrombosis, thromboembolism and reocclusion during and after thrombolytic therapy. Since blood vessels can also sustain chronic damage by the pathophysiological processes of atherosclerosis, patients with atherosclerosis can also be treated with the formulations provided herein to prevent or reduce the risk of occlusive thrombus formation.

The formulations and methods provided herein can also be used to treat, prevent or reduce the risk of a first or subsequent myocardial infarction in a person at risk for such events as well as to prevent or reduce the risk of restenosis in persons at risk for restenosis. Additionally, the formulations and methods provided herein can be used for treating, preventing or reducing the risk of occurrence of acute cerebrovascular ischemic events (e.g. a first or subsequent thrombotic stroke, or transient ischemic attack).

The formulations and methods provided herein can also be used to treat, prevent or reduce the risk of a gastrointestinal disorder or future reoccurrence thereof, or reducing the severity, duration, and/or symptoms of the gastrointestinal disorder. The gastrointestinal disorder can be any in the art, and includes gastrointestinal disorders associated with antiplatelet agents, such as NSAIDs. The gastrointestinal disorder includes, without limitation, ulcers, such as peptic ulcers including gastric ulcers and duodenal ulcers, bleeding peptic ulcers, stress ulcers, stomal ulcers, refractory ulcers, esophageal ulcers, bacterial-induced ulcers, such as *H. pylori*, fungal-induced ulcers, viral-induced ulcers, and the like.

As described above, a major factor contributing to the development of gastrointestinal disorders is the presence of acid in the stomach and upper small intestine. Therefore, administering to a subject an oral dosage form including a combination of an antiplatelet agent and an acid inhibitor can reduce a major factor contributing to the development of gastrointestinal disorder in subjects. In general, the method comprises orally administering to a subject a dosage form comprising in combination a therapeutically effective amount of an antiplatelet agent and an acid inhibitor. Likewise orally co-administering one or more antiplatelet agents and one or more acid inhibitors can reduce a major factor contributing to the development of gastrointestinal disorder in subjects. The method comprises orally co-administering to a subject one or more antiplatelet agents and one or more acid inhibitors.

In some embodiments, the patient does not have a gastrointestinal disorder, such as bleeding and/or ulcers. In such embodiments, the patient can be diagnosed by a physician as not having a gastrointestinal disorder and is orally administered a dosage form comprising in combination a therapeutically effective amount of an antiplatelet agent and an acid inhibitor. Alternatively, in some embodiments, the patient has a gastrointestinal disorder, such as bleeding and/or ulcers. In such embodiments, the patient is diagnosed as having a gastrointestinal disorder and is orally administered a dosage form comprising in combination a therapeutically effective amount of an antiplatelet agent and an acid inhibitor. In a specific embodiment, the oral dosage form is administered for the purpose of decreasing the onset or progression of ulcers, bleeding, and/or increasing the ability of the subject to heal ulcers or nascent pre-ulcer lesions.

In some embodiments, the subject is diagnosed as having a gastrointestinal disorder and is orally administered, either as a single unit or as multiple units in a single package, a combination of a therapeutically effective amount of an antiplatelet agent and an acid inhibitor. In a specific embodiment, the antiplatelet agent and an acid inhibitor are co-administered for the purpose of decreasing the onset or progression of ulcers, bleeding, and/or increasing the ability of the subject to heal ulcers or nascent pre-ulcer lesions.

Also provided is a method to treat, prevent or reduce the risk of a gastrointestinal disorder associated with an NSAID therapy in a subject. For example, the administration of NSAIDs can lead to the development of gastroduodenal lesions, e.g., ulcers and erosions, in susceptible individuals. A major factor contributing to the development of these lesions is the presence of acid in the stomach and upper small intestine of patients, see for example Drug Safety 21:503-512 (1999); Aliment. Pharmacol. Ther. 12:135-140 (1998); Am. J. Med. 104(3A),67S-74S (1998); Clin. Ther. 17:1159-1173 (1995)). The method comprises orally administering to a subject, either as a single unit or as multiple units in a single package, a therapeutically effective amount of an antiplatelet agent in combination with an acid inhibitor.

The formulations and methods provided herein are advantageous in minimizing or avoiding gastrointestinal disorders associated with antiplatelet agents, such as in a continuous treatment with antiplatelet agents. The formulations can be administered one to several times a day. The methods can be performed one to several times a day. The daily dose of the active substances varies and will depend on various factors such as the individual requirements of the patients, properties of the actives, the mode of administration and disorder.

In some embodiments, the oral dosage form comprises clopidogrel or prasugrel in combination with omeprazole, esomeprazole or lansoprazole and can be administered to patients for whom treatment with PLAVIX™ (clopidogrel bisulfate) is appropriate. In a specific embodiment, the oral dosage form comprises clopidogrel or prasugrel in combination with omeprazole, esomeprazole or lansoprazole and can be administered to patients to reduce the incidence of gastrointestinal events in patients for whom treatment with PLAVIX™ is indicated for the reduction of thrombotic events including recent myocardial infarction (MI), recent stroke or established peripheral arterial disease, and reduce the rate of a combined endpoint of new ischemic stroke (fatal or not), new MI (fatal or not), and other vascular death. For patients with acute coronary syndrome (unstable anginainon-Q-wave MI), including patients who are to be managed medically and those who are to be manned with percutaneous coronary intervention (with or without stent) or CABG, PLAVIX™ has been shown to decrease the rate of a combined endpoint of cardiovascular death, MI, or stroke as well as the rate of a combined endpoint of cardiovascular death, MI, stroke, or refractory ischemia.

In some embodiments, the method comprises orally administering to a subject, either as a single unit or as multiple units in a single package, clopidogrel or prasugrel in combination with omeprazole, esomeprazole or lansoprazole. Generally, orally co-administering clopidogrel and omeprazole is appropriate in patients for whom treatment with PLAVIX™ (clopidogrel bisulfate) is appropriate. In a specific embodiment, the method comprises orally administering, either as a single unit or as multiple units in a single package, clopidogrel and omeprazole to patients to reduce the incidence of gastrointestinal events in patients for whom treatment with PLAVIX™ is indicated for the reduction of thrombotic events including recent myocardial infarction (MI), recent stroke or established peripheral arterial disease, and reduce the rate of a combined endpoint of new ischemic stroke (fatal or not), new MI (fatal or not), and other vascular death. For patients with acute coronary syndrome (unstable angina/non-Q-wave MD, including patients who are to be managed medically and those who are to be managed with percutaneous coronary intervention (with or without stent) or CABG, PLAVIX™ has been shown to decrease the rate of a combined endpoint of cardiovascular death, MI, or stroke as well as the rate of a combined endpoint of cardiovascular death, MI, stroke, or refractory ischemia.

In another exemplary embodiment, the invention provides a method of preventing or reducing the severity, duration, and/or symptoms of a gastrointestinal disorder associated with an antiplatelet agent in a patient comprising orally administering to said patient an oral dosage form comprising a therapeutically effective amount of a first active ingredient, wherein said first active ingredient is an antiplatelet agent, and a therapeutically effective amount of a second active ingredient, wherein said second active ingredient is an acid inhibitor. In an exemplary embodiment, the antiplatelet agent is clopidogrel and the acid inhibitor is a member selected from omeprazole, esomeprazole and lansoprazole. In an exemplary embodiment, the antiplatelet agent is prasugrel and the acid inhibitor is a member selected from omeprazole, esomeprazole and lansoprazole.

In another exemplary embodiment, the invention provides a method of preventing or reducing the severity, duration, and/or symptoms of a gastrointestinal disorder associated with an antiplatelet agent in a patient comprising orally co-administering to said patient an oral dosage form comprising a therapeutically effective amount of a first active ingredient, wherein said first active ingredient is an antiplatelet agent, and a therapeutically effective amount of a second active ingredient, wherein said second active ingredient is an acid inhibitor, and a third active ingredient, wherein said third active ingredient is aspirin. In an exemplary embodiment, the antiplatelet agent is clopidogrel and the acid inhibitor is a member selected from omeprazole, esomeprazole and lansoprazole. In an exemplary embodiment, the antiplatelet agent is prasugrel and the acid inhibitor is a member selected from omeprazole, esomeprazole and lansoprazole.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

All patents, patent applications, publications, and references cited herein are expressly incorporated by reference to the same extent as if each individual publication or patent application was specifically and individually indicated to be incorporated by reference.

EXAMPLES

Aspects of the present teachings may further be understood in light of the following examples, which should not be construed as limiting the scope of the present teachings in any way.

For this Examples section only, unless specifically states, discussions of antiplatelet agents and acid inhibitors does not encompass their pharmaceutically acceptable salts, polymorphic crystal forms including the amorphous form, solvates, hydrates, co-crystals, complexes, active metabolites, active derivatives and modifications, or pro-drugs. For example, 'clopidogrel' in this Examples section refers only to the molecule itself without a corresponding salt, whereas "clopidogrel bisulphate' refers to the antiplatelet agent clopidogrel and its salt bisulphate.

Example 1

Synthesis of Thienopyridine Antiplatelet Agents a) Synthesis of Clopidogrel for Oral Dosage Forms Clopidogrel can be synthesized as described in U.S. Pat. No. 4,529,596. 1 eq. of methyl 2-chloro-orthochlorophenylacetate and 1 eq. of potassium carbonate are added to a solution containing 1 eq. of 4,5,6,7-tetrahydro thieno[3,2-c] pyridine in 200 mL of dimethylformamide. The solution is then heated for four hours at 90° C. The reaction mixture is cooled to room temperature, the mineral salts are filtered and the solvent is evaporated. The residue is taken up in water and then extracted with ethylic ether. The ether extracts are washed with water, dried over sodium sulphate and evaporated, to give a yellow oil which is purified by means of its hydrochloride. White crystals: M.p.=130-140° C. (ethylacetate, isopropanol), Yield: 45%.

The process created enantiomers, which can be separated according to the methods described in U.S. Pat. No. 4,847,265.

b) Synthesis of Prasugrel for Oral Dosage Forms

Prasugrel (2-acetoxy-5-(α-cyclopropylcarbonyl-2-fluorobenzyl)-4,5,6,7-tetrahydro thieno[3,2-c]pyridine) can be produced according to the methods described in U.S. Pat. No. 6,693,115. One method of production is described here:

2-Acetoxy-5-(α-cyclopropylcarbonyl-2-fluorobenzyl)-4,5,6,7-tetrahydro thieno[3,2-c]pyridine (a) Cyclopropyl 2-fluorobenzyl ketone To a suspension of magnesium powder (7.2 g) in anhydrous diethyl ether (60 ml) was added a solution of 2-fluorobenzylbromide (30 ml) in diethyl ether (30 ml), then the mixture was stirred at room temperature for 1 hour. The reaction mixture was added dropwise to a solution of cyclopropyl cyamide (18.2 mL) in diethyl ether (120 mL) over 100 minutes. After stirring for 30 minutes at room temperature the stirred mixture was heated under reflux for 1 hour. After the reaction, the reaction mixture was partitioned between ethyl acetate and saturated aqueous ammonium chloride solution. The ethyl acetate layer washed successively with water, saturated aqueous sodium bicarbonate solution, and saturated aqueous sodium chloride solution, then dried over anhydrous sodium sulfate, and then evaporated under reduced pressure. The residue was purified by chromatography on a silica gel column using toluene as the eluant to afford the desired product (23 g containing solvent) as a yellow liquid. $^1$H NMR (CDCl$_3$) δ ppm: 0.82-0.98 (2H, m), 1.03-1.17 (2H, m), 1.92-2.06 (1H, m), 3.86 (2H, s), 7.10-7.30 (4H, m); Mass (CL, m/z): 179 (M.sup.++1).

(b) 5-(α-Cyclopropylcarbonyl-2-fluorobenzyl)-2-oxo-2,4,5,6,7,7a-hexahydrothieno[3,2-c]pyridine To a solution of cyclopropyl 2-fluorobenzyl ketone (8.7 g) obtained in part (a) in carbon tetrachloride (80 ml) was added N-bromosuccinimide (9.6 g) and benzoyl peroxide (0.5 g), then the mixture was heated under reflux for 6 hours. After the reaction, toluene was added to the reaction mixture and the resulting solid was filtered off. The filtrate was concentrated under reduced pressure. The residue was purified by chromatography on a silica gel column using toluene as the eluant to afford α-cyclopropylcarbonyl-2-fluorobenzyl bromide (8.5 g) as a yellow oil.

To a solution of α-cyclopropylcarbonyl-2-fluorobenzyl bromide (6.0 g) obtained above in dimethylformamide (20 mL) was added 2-oxo-2,4,5,6,7,7a-hexahydrothieno[3,2-c]pyridine hydrochloride (4.8 g), which was prepared according to the method described in EP 192535 (Japanese Patent Application Publication No. Sho 61-246186) and potassium bicarbonate (7.0 g). After stirring the mixture at room temperature for 2 hours the reaction mixture was partitioned between ethyl acetate and water. The ethyl acetate layer washed with saturated aqueous sodium chloride solution, then dried over anhydrous magnesium sulfate, and evaporated under reduced pressure. After purification of the residue by chromatography on a silica gel column using toluene/ethyl acetate=3/1 as the eluant, the product was crystallized from diisopropyl ether to afford the desired product (2.6 g, yield 35%) as pale brown crystals. $^1$H NMR (CDCl$_3$) δ ppm: 0.75-0.96 (2H, m), 0.99-1.14 (2H, m), 1.83-2.01 (1H, m), 2.02-2.17 (1H, m), 2.25-2.45 and 2.47-2.62 (total 2H, each m), 2.85 and 3.10 (total 2H, each d, J=12.0 Hz), 3.88-4.01 and 4.03-4.16 (total 2H, each m), 4.85 and 4.89 (total 1H, each s), 6.03 and 6.06 (total 1H, each s), 7.10-7.45 (4H, m). Mass (Cl, m/z):332 (M.sup.++1), 262; Anal Calcd. for C$_{18}$H$_{18}$FNO$_2$S: C, 65.23; H, 5.48; N, 4.23. Found: C, 65.09; H, 5.55; N, 4.20.

(c) 2-Acetoxy-5-(α-cyclopropylcarbonyl-2-fluorobenzyl)-4,5,6,7-tetrahydrothieno[3,2-c]pyridine To a solution of 5-(α-cyclopropylcarbonyl-2-fluorobenzyl)-2-oxo-2,4,5,6,7,7a-hexahydro thieno[3,2-c]pyridine (2.6 g) obtained in reference part (b) in a mixture of dimethylformamide (10 ml) and acetic anhydride (5 ml), cooled in an ice bath, was added sodium hydride (60% dispersion in mineral oil, 0.35 g), then the mixture was stirred at the same temperature for 30 minutes, and then at room temperature for 3 hours. After the reaction, the mixture was extracted with ethyl acetate and the extract washed with saturated aqueous sodium chloride solution, then dried over anhydrous sodium sulfate, and concentrated under reduced pressure. After purification of the residue by chromatography on a silica gel column using toluene/ethyl acetate=3/1 as the eluant, the product was crystallized from diisopropyl ether to afford the title compound (1.88 g, yield 65%) as white crystals. Mp: 120-122° C.; $^1$H NMR (CDCl$_3$) δ ppm: 0.80-0.95 (2H, m), 0.99-1.16 (2H, m), 2.27 (3H, s), 2.21-2.34 (1H, m), 2.70-2.95 (4H, m), 3.47 (1H, d, J=15.0 Hz), 3.57 (1H, d, J=15.0 Hz), 4.83 (1H, s), 6.27 (1H, s), 7.10-7.55 (4H, m); Mass (Cl, m/z): 374 (M.sup.++1), 304; Anal Calcd. for C$_{20}$H$_{20}$FNO$_3$S: C, 64.32; H, 5.40; N, 3.75. Found: C, 64.46; H, 5.39; N, 3.73.

Example 2

Making Acid Agents

Several prototype capsule formulations were created and are described in the following table.

| | Prototype Formulations for CGT-2168 Capsules | | | | | |
|---|---|---|---|---|---|---|
| | Batch # | | | | | |
| | 1 | | 2 | | 3 | |
| | Capsule Strength | | | | | |
| | 75/10 | | 75/20 | | 75/40 | |
| Component | mg/capsule | % w/w | mg/capsule | % w/w | mg/capsule | % w/w |
| Omeprazole Enteric Coated Pellets, 8.5% | 117.00 * | 41.49 | 233.00 * | 63.32 | 466.00 * | 65.09 |
| Clopidogrel Blend | 165.00 | 58.51 | 135.00 | 36.68 | 250.00 | 34.91 |
| Total (mg) | 282.00 | 100 | 368.00 | 100 | 716.00 | 100 |
| Capsule size | 2 | | 1 | | 00 | |
| Average empty | 0.06190 g, | | 0.07674 g, | | 0.11503 g, | |

-continued

Prototype Formulations for CGT-2168 Capsules

| | Batch # | | | | |
|---|---|---|---|---|---|
| | 1 | | 2 | | 3 |
| | | | Capsule Strength | | |
| | 75/10 | | 75/20 | | 75/40 |
| Component | mg/capsule | % w/w | mg/capsule | % w/w | mg/capsule | % w/w |
| capsule weight (n = 50), RSD | 1.73% | | 1.80% | | 1.13% | |
| Theoretical target weight | 343.9 mg | | 444.7 mg | | 831.0 mg | |

\* These amount were based on 8.59% Omeprazole in the Enteric Coated Pellets (supplier's CoA).

Example 3

Clopidogrel/Omeprazole Capsules (75 mg Clopidogrel/40 mg Omeprazole)

The components of clopidogrel/omeprazole 75/40 capsules are provided in Table 1.

TABLE 1

Qualitative Composition of clopidogrel/omeprazole 75/40 capsules

| Component | Description/Function | Reference to Standard |
|---|---|---|
| Clopidogrel Bisulphate | Active | USP |
| Omeprazole Pellets 8.5% | Active | USP |
| Excipients: | | |
| Mannitol Powder | Filler | USP/EP |
| Microcrystalline Cellulose NF CRS (PH102) | Filler/Disintegrant | NF/EP/JP |
| Hydroxypropylcellulose | Binder | USP/NF |
| Polyethylene Glycol 6000 | Glidant | USP/EP |
| Hydrogenated Castor Oil | Lubricant | USP/EP |
| #00 White Opaque Capsule | Container | Capsugel In-house |

The inactive components of clopidogrel/omeprazole 75/40 capsules were tested according to the analytical methods and complied with the specifications listed in their pharmacopoeial monographs.

All of the inactive ingredients used in the manufacture of clopidogrel/omeprazole 75/40 capsules are compendial and appear in the FDA's Inactive Ingredients Guide (IIG). Table 2 below shows the amount of each ingredient in clopidogrel/omeprazole 75/40 capsules (administered once daily) and the maximum amount of that ingredient in an oral formulation listed in the IIG. All excipients are well below the amounts listed in the IIG.

TABLE 2

Review of Excipients in clopidogrel/omeprazole 75/40 capsules

| Ingredient | mg/capsule clopidogrel/omeprazole 75/40 capsules | Maximum Amount in an Oral Formulation in the IIG (mg) |
|---|---|---|
| Mannitol Powder | 62.0 | 500.0 |
| Microcrystalline Cellulose (PH102) | 24.0 | 363.8 |

TABLE 2-continued

Review of Excipients in clopidogrel/omeprazole 75/40 capsules

| Ingredient | mg/capsule clopidogrel/omeprazole 75/40 capsules | Maximum Amount in an Oral Formulation in the IIG (mg) |
|---|---|---|
| Hydroxypropylcellulose EP | 8.0 | 71.3 |
| Polyethylene Glycol 6000 | 6.0 | 450.0 |
| Hydrogenated Castor Oil | 2.0 | 405.0 |

Mannitol powder was supplied by SPI Polymers (New Castle, Del.). Microcrystalline Cellulose was supplied by FMC BioPolymer (Wallingstown, Cork, Ireland). Hydroxypropylcellulose EP was supplied by Hercules, Aqualon Division (Hopewell, Va.). Polyethylene Glycol 6000 was supplied by Clariant Corporations Detergents (Mt. Holly, N.C.). Hydrogenated Castor Oil was supplied by Cognis Deutschland Gmbh. (Dusseldorf, Germany) The capsule used in the invention was #00 White Opaque Capsule produced by Capsugel (Greenwood, S.C.).

Quantitative Composition

The quantitative composition of clopidogrel/omeprazole 75/40 capsules is presented in Table 3.

TABLE 3

Quantitative Composition of clopidogrel/omeprazole 75/40 capsules

| Ingredient | % w/w | mg/capsule |
|---|---|---|
| Clopidogrel Bisulfate | 49.0 | 98.0 |
| Mannitol Powder | 31.0 | 62.0 |
| Microcrystalline Cellulose (PH102) | 12.0 | 24.0 |
| Hydroxypropylcellulose EP | 4.0 | 8.0 |
| Polyethylene Glycol 6000 | 3.0 | 6.0 |
| Hydrogenated Castor Oil | 1.0 | 2.0 |
| Total Blend: | 100.0 | 200.0 |
| Total Blend: | 29.8 | 200.0 |
| Omeprazole Pellets 8.5% | 70.2 | 471.0 |
| Total in Capsule: | 100.0 | 671.0 |

Characterization/Development of Clopidogrel/Omeprazole 75/40 Capsules

Excipients were selected based primarily on the inactive components contained in the commercial clopidogrel bisulfate formulation. A formal drug excipient study of 12 weeks duration was carried out using mixtures of clopidogrel bisulfate, a single excipient and enteric coated omeprazole pellets 8.5%. In addition to the excipients used in the commercial formulation, some commonly used excipients were also tested. Stress conditions were 40° C./75% RH and samples were tested initially and at 1, 2, 4, 6, 8 and 12 weeks. Samples were stored also at 25° C./60% RH to be tested only if the stress sample failed. Clopidogrel bisulfate and enteric coated omeprazole pellets 8.5%, each alone and in combination, were stored under the same conditions and served as controls.

Several prototype formulations were developed for a manual gelatin capsule filling process. Table 4 summarizes the prototype formulations for the clopidogrel bisulfate blend and the composition of the clopidogrel/omeprazole capsule.

The following formulations are for a capsule containing two ingredients in a capsule—clopidogrel (75 mg) and enteric coated omeprazole pellets (10 mg, 20 mg, 40 mg) with an 8.5% loading in the pellets.

Example 4

Manufacturing and Packaging Procedures for Clopidogrel/Omeprazole Capsules (75 mg Clopidogrel/40 mg Omeprazole)

A description of the manufacturing processes for clopidogrel/omeprazole 75/40 capsules is provided in this section.

Clopidogrel Blend

The following ingredients are passed through a #20 mesh screen prior to dispensing to the batch: clopidogrel bisulfate, mannitol powder USP/EP, microcrystalline cellulose NF (PH 102), hydroxypropylcellulose EP, polyethylene glycol 6000 and hydrogenated castor oil.

If the potency of the lot of clopidogrel bisulfate used is less than 100%, the amount of clopidogrel bisulfate is adjusted for potency prior to dispensing as per the batch record. The extra amount of clopidogrel bisulfate added to

TABLE 4

Formulations for Clopidogrel/Omeprazole Capsules

| | Clopidogrel/Omeprazole Dose | | | | | |
|---|---|---|---|---|---|---|
| | 75/10* | | 75/20* | | 75/40* | |
| Component | % w/w | mg/capsule | % w/w | mg/capsule | % w/w | mg/capsule |
| Clopidogrel Bisulfate | 59.39 | 98.00 | 72.59 | 98.00 | 39.20 | 98.00 |
| Mannitol | 20.61 | 34.00 | 7.41 | 10.00 | 40.80 | 102.00 |
| Microcrystalline Cellulose | 12.00 | 19.80 | 12.00 | 16.20 | 12.00 | 30.00 |
| Hydroxypropylcellulose | 4.00 | 6.60 | 4.00 | 5.40 | 4.00 | 10.00 |
| Polyethylene Glycol 6000 | 3.00 | 4.95 | 3.00 | 4.05 | 3.00 | 7.50 |
| Hydrogenated Castor Oil | 1.00 | 1.65 | 1.00 | 1.35 | 1.00 | 2.50 |
| Total Clopidogrel Blend: | 100.0 | 165.00 | 100.0 | 135.00 | 100.0 | 250.00 |
| Clopidogrel Blend | 58.51 | 165.00 | 36.68 | 135.00 | 34.91 | 250.00 |
| Omeprazole Pellets 8.5% ** | 41.49 | 117.00 | 63.32 | 233.00 | 65.09 | 466.00 |
| Total Fill: | 100.0 | 282.00 | 100.0 | 368.00 | 100.0 | 716.00 |
| Gelatin Capsule Size | 2 | | 1 | | 00 | |
| Average Empty Capsule Weight (N = 50), RSD | 61.9 mg , 1.73% | | 76.7 mg , 1.80% | | 115.0 mg, 1-13% | |
| Total Capsule Weight (mg): | 343.9 | | 444.7 | | 831.0 | |

*First number represents dosage of clopidogrel bisulfate in capsule and second number represents dosage of omeprazole in capsule.
** The amount of omeprazole pellets 8.5% was based on the potency provided on the manufacturer's Certificate of Analysis (8.59%).

For consistency, the relative amounts of the following excipients were fixed across all prototype formulations; microcrystalline cellulose at 12.0%, hydroxypropylcellulose at 4.0%, polyethylene glycol 6000 at 3.0% and hydrogenated castor oil at 1.0%. The formulations differed only in the quantity of the filler mannitol and the omeprazole pellets 8.5%.

Based on the potency of the clopidogrel bisulfate and the omeprazole pellets 8.5% (both of which were below 100%), the formulation for the clopidogrel/omeprazole 75/40 capsules was adjusted to the formulation listed in Table 7, as the fill volume of the materials exceeded the capacity of the Size 00 gelatin capsule. The reduction in the amount of mannitol in the 75/40 formulation from 102.0 mg to 62.0 mg is bracketed by the range used in the prototype formulations.

the batch is calculated and an equivalent weight of mannitol is removed to maintain a powder blend fill of 200 g.

The materials are charged in the following order into a 4-qt V-shell blender and blended for 10 minutes at 25 rpm: clopidogrel bisulfate, mannitol powder USP/EP, microcrystalline cellulose NF (PH 102), hydroxypropylcellulose EP and polyethylene glycol 6000. After the 10 minute preblend, the hydrogenated castor oil is added and the material mixed for an additional 3 minutes at 25 rpm. The final blend is discharged into a container lined with double polyethylene bags.

Capsule Filling

If the potency of the lot of omeprazole pellets 8.5% used is less than 100%, the amount of omeprazole pellets 8.5% is adjusted for potency prior to dispensing as per the batch record. The potency adjusted amount of omeprazole pellets 8.5% to be weighed and charged into each gelatin capsule is calculated.

The average weight of one empty size 00 gelatin capsule is determined by weighing 100 randomly selected capsules. The theoretical gross weight of an individual filled capsule (and 30 filled capsules) is calculated by adding the average weight of one empty capsule plus the potency adjusted weight of the omeprazole pellets 8.5% and 0.200 g of clopidogrel blend (all multiplied by 30 for the 30 filled capsules). The filled capsule limits are calculated (±3% of the gross filled weight of 1 or 30 capsules) and recorded on the Encapsulation Record. The relative standard deviation on the individual filled capsule weight is ≤5.0%.

The empty gelatin capsules are loaded into a capsule holding plate of the MF-30 manual capsule filler using the AL-90 Automatic Capsule Loader. The potency adjusted amount of omeprazole pellets 8.5% (±1%) is manually weighted and transferred into each gelatin capsule. Once all 300 capsules in the capsule holding tray are filled with omeprazole pellets 8.5%, the clopidogrel blend is evenly distributed over all the capsules. (Note: The blend is filled into the omeprazole pellet loaded capsules by volume.)

Once encapsulated, the filled capsules are ejected from the MF-30 Manual Capsule Filler into a polyethylene lined plastic holding container. From each tray of 300 filled capsules, 30 randomly selected capsules are sampled for individual weight checks. If one or more capsules fail the individual weight variation test, a 100% weight check is performed on the entire tray of capsules.

Example 5

Analytical Methods for Oral Dosage Forms

The following four analytical methods and two USP methods were used in testing the clopidogrel/omeprazole 75/40 capsules.
Determination of the Enteric Integrity for Omeprazole Pellets and Omeprazole Pellets in Clopidogrel/Omeprazole 75/40 Capsules:

The enteric integrity for omeprazole pellets and omeprazole pellets in clopidogrel/omeprazole 75/40 capsules was tested. The omeprazole pellets in the clopidogrel/omeprazole 75/40 capsules were subjected to dissolution media 0.1N HCl for two hours. Quantitation of the remaining omeprazole was performed using reverse phase liquid chromatography with ultraviolet detection at 280 nm. It was determined that not more than 10% of omeprazole dissolved in the clopidogrel/omeprazole 75/40 capsules.
Dissolution Assay of Clopidogrel and Omeprazole in Clopidogrel/Omeprazole 75/40 Capsules:

The dissolution profiles for clopidogrel bisulfate and omeprazole from clopidogrel/omeprazole 75/40 capsules were determined using USP Apparatus 1. The dissolution media was 0.1N HCl for clopidogrel bisulfate followed by 0.05M phosphate buffer for omeprazole. Samples were taken for both clopidogrel bisulfate and omeprazole at 10, 15, 30, 45 and 60 minutes. Quantitation was performed using reverse phase liquid chromatography with ultraviolet detection at 220 nm for clopidogrel bisulfate and 280 nm for omeprazole.
Identification of Clopidogrel Bisulfate and Determination of Clopidogrel Bisulfate and Related Substances in Clopidogrel/Omeprazole 75/40 Capsules:

The content of clopidogrel bisulfate, identification of clopidogrel bisulfate and determination of related substances of clopidogrel bisulfate in clopidogrel/omeprazole 75/40 capsules was determined. The clopidogrel bisulfate and related substances were extracted into prepared diluent. Quantitation was performed using reverse phase liquid chromatography with ultraviolet detection at 220 nm. The retention time of the main peak in the sample preparation corresponds to that in the standard preparation.
Identification of Omeprazole and Determination of Omeprazole and Related Substances in Clopidogrel/Omeprazole 75/40 Capsules:

The content of omeprazole, identification of omeprazole and determination of related substances of omeprazole in clopidogrel/omeprazole 75/40 capsules was determined. The omeprazole and related substances were extracted into prepared diluent. Quantitation was performed using reverse phase liquid chromatography with ultraviolet detection at 280 nm. The retention time of the main peak in the sample preparation corresponds to that in the standard preparation.

Example 6

Excipient Compatibility Study Report for Clopidogrel/Omeprazole Capsules

The purpose of this study was to evaluate potential excipients with the active pharmaceutical ingredients (APIs), Clopidogrel Bisulfate and Omeprazole Enteric Coated Pellets, for the formulation of 75/10, 75/20, and 75/40 mg clopidogrel/omeprazole capsules according to the Excipient Compatibility Protocol VAL 1790.

The development work explored the compatibility of both APIs together with each of the proposed excipients individually in different ratios depending on the function of the excipient at different temperature and humidity conditions.

Samples were evaluated for Clopidogrel Bisulfate potency recovery, % w/w of drug related impurities and physical appearance. The potency of Omeprazole in the EC Pellets was not evaluated in the samples because the Omeprazole was presumably protected by the enteric coating and should not be affected by interaction with the excipients.

The selected excipients were mixed with the APIs in different ratios depending on the excipient functionality (Table 5). In addition, samples of pure APIs and excipients were prepared and provided as reference and control respectively. All samples were placed in clear glass vials with screwed on plastic caps and stored at the following storage conditions:

40° C./75% RH
25° C./60% RH
5° C./ambient RH

TABLE 5

Ratio of Omeprazole Enteric Coated Pellet to Clopidogrel Bisulfate to Various Excipients

| Excipient | Function | Absolute Ratio of Omeprazole Enteric Coated Pellets:Clopidogrel Bisulfate:Excipient |
|---|---|---|
| Mannitol | Filler | 1.00:0.40:1.20 |
| Microcrystalline Cellulose | Filler/Disintegrant | 1.00:0.40:0.40 |
| Hydroxypropylcellulose | Binder | 1.00:0.40:0.20 |
| Polyethylene Glycol 6000 | Lubricant | 1.00:0.40:0.10 |
| Hydrogenated Castor Oil | Lubricant | 1.00:0.40:0.06 |

TABLE 5-continued

Ratio of Omeprazole Enteric Coated Pellet to Clopidogrel Bisulfate to Various Excipients

| Excipient | Function | Absolute Ratio of Omeprazole Enteric Coated Pellets:Clopidogrel Bisulfate:Excipient |
|---|---|---|
| Povidone K 29-32 | Binder | 1.00:0.40:0.20 |
| Lactose 316 Fast Flo (monohydrate) | Filler | 1.00:0.40:1.20 |
| Croscarmellose Sodium | Disintegrant | 1.00:0.40:0.20 |
| Hydroxypropylmethyl cellulose | Binder/Filler | 1.00:0.40:0.40 |
| White/White Opaque Capsule | Capsules | 1.00:0.40:1 capsule (cut in pieces) |

The samples were tested for physical appearance, % drug (Clopidogrel Bisulfate) recovery and drug related substances/degradation products (if any) by HPLC according to Table 6.

TABLE 6

Storage Conditions, Closure Type and Time points for Testing of Drug Substances: Excipient, Drug Substances alone and Excipients alone

| Sample | Storage Condition | Closure type | Time point, weeks | | | | | | |
|---|---|---|---|---|---|---|---|---|---|
| | | | 0 | 1 | 2 | 4 | 6 | 8 | 12 |
| Drug Substances and Excipient mixture | 40° C./75% RH | Plastic cap | A | A | A | A | A | A | A |
| | 25° C./60% RH | Plastic cap | | B | B | B | B | B | B |
| | 5° C./ambient RH | Plastic cap | | B | B | B | B | B | B |
| Drug substance | 40° C./75% RH | Plastic cap | A | A | A | A | A | A | A |
| | 25° C./60% RH | Plastic cap | | B | B | B | B | B | B |
| | 5° C./ambient RH | Plastic cap | | B | B | B | B | B | B |
| Excipient | 40° C./75% RH | Plastic cap | O | O | O | O | O | O | O |
| | 25° C./60% RH | Plastic cap | | O | O | O | O | O | O |
| | 5° C./ambient RH | Plastic cap | | O | O | O | O | O | O |

A = Testing conducted
B = Test if the 40° C./75% RH testing results do not meet the acceptance criteria.
O = Optional testing The physical appearance, % recovery of Clopidogrel Bisulfate and % w/w of related substances for each sample were evaluated. The results of the physical appearance of each mixture are presented in Table 7. The % of Clopidogrel Bisulfate recovered is summarized in Table 8.

TABLE 7

Physical Appearance of Samples stored at 40° C./75% RH

| Set # | | Initial | 1 | 2 | 4 | 6 | 8 | 12 |
|---|---|---|---|---|---|---|---|---|
| 1 | Mannitol | T | T | T | T | V | W | Z |
| 2 | Microcrystalline Cellulose | T | T | T | T | S | W | W |
| 3 | Hydroxypropyl-cellulose | T | T | T | R | V | Q | P |
| 4 | Polyethylene Glycol 6000 | T | T | T | T | V | O | W |
| 5 | Hydrogenated Castor Oil | T | T | T | T | V | W | O |
| 6 | Povidone K 29-32 | T | T | T | T | N | W | W |
| 7 | Lactose 316 Fast Flo (monohydrate) | T | T | T | T | V | Q | W |
| 8 | Croscarmellose Sodium | T | T | T | M | L | N | Not Tested |
| 9 | Hydroxypropyl methylcellulose | T | T | K | K | V | W | J |
| 10 | White/White Opaque Capsule | T | Y | T | T | I | H | I |
| 11 | Clopidogrel Bisulfate (control reference) | X | X | X | X | X | X | X |

TABLE 7-continued

Physical Appearance of Samples stored at 40° C./75% RH

| Set # | | Initial | 1 | 2 | 4 | 6 | 8 | 12 |
|---|---|---|---|---|---|---|---|---|
| 12 | Omeprazole enteric coated pellets | Omeprazole pellets | Omeprazole pellets | Omeprazole pellets | Omeprazole pellets | Off White pellets | Off White pellets | Off White pellets |
| 13 | Clopidogrel Bisulfate; Omeprazole enteric Coated Pellets (Control reference) | T | T | T | T | V | W | W |

T: Off white powder with pellets
V: Off white powder with white pellets
W: Off white powder with off white pellets
X: Off white powder without pellets
Y: Off white powder with pellets and shells
Z: Sticky off white powder with grey pellets
S: Off white powder with blue pellets
R: Off white powder with grey pellets
Q: Off white powder with brown pellets
P: Brownish sticky powder with gray pellets
O: Off white powder with sticking brown pellets
N: Brownish sticky powder with blue pellets
M: Slight yellow powder with grey pellets
L: Light brownish sticky powder with off white pellets
K: Slight yellow agglutinate
J: Sticky off white powder with off white pellets
I: Capsule shells with white pellets and off white powder
H: Capsule shells with yellowish pellets and off white powder

TABLE 8

% Recovery of Clopidogrel Bisulfate for Samples Stored at 40° C./75% RH

| Set # | | Initial | 1 | 2 | 4 | 6 | 8 | 12 |
|---|---|---|---|---|---|---|---|---|
| | | | | Clopidogrel Bisulfate % Recovery | | | | |
| 1 | Mannitol | 94.8 | 97.2 | 97.2 | 94.3 | 93.8 | 96.3 | 93.5 |
| 2 | Microcrystalline Cellulose | 95.5 | 99.0 | 101.1 | 95.7 | 94.0 | 95.4 | 98.0 |
| 3 | Hydroxypropylcellulose | 94.0 | 97.7 | 98.5 | 95.2 | 96.5 | 98.0 | 93.1 |
| 4 | Polyethylene Glycol 6000 | 105.4 | 98.2 | 97.4 | 93.8 | 95.5 | 98.4 | 98.8 |
| 5 | Hydrogenated Castor Oil | 95.7 | 99.9 | 99.1 | 95.9 | 98.1 | 99.2 | 100.5 |
| 6 | Povidone K 29-32 | 97.0 | 99.0 | 97.8 | 96.1 | 77.9 | 97.6 | 99.8 |
| 7 | Lactose 316 Fast Flo (monohydrate) | 94.7 | 96.1 | 97.0 | 94.2 | 95.1 | 95.8 | 97.2 |
| 8 | Croscarmellose Sodium | 92.6 | 96.2 | 96.7 | 84.2 | 88.6 | 85.3 | — |
| 9 | Hydroxypropylmethylcellulose | 89.4 | 96.8 | 96.4 | 96.2 | 94.6 | 91.1 | 93.4 |
| 10 | White/White Opaque Capsule | 95.7 | 100.3 | 96.0 | 96.4 | 95.8 | 93.8 | 99.3 |
| 11 | Clopidogrel Bisulfate (control reference) | 96.5 | 99.5 | 97.5 | 96.3 | 95.9 | 98.3 | 96.0 |
| 13 | Clopidogrel Bisulfate: Omeprazole enteric Coated Pellets (Control reference) | 96.4 | 99.6 | 97.9 | 97.5 | 96.8 | 98.4 | 97.1 |

Based on the results as summarized in Tables 7 and 8, the excipient which showed the greatest degree of incompatibility with Clopidogrel Bisulfate and Omeprazole EC Pellets was Croscarmellose Sodium. When Omeprazole EC Pellets, Clopidogrel Bisulfate and Croscarmellose Sodium were mixed at a ratio of 1.00:0.40:0.20, the % recovery of Clopidogrel Bisulfate was found to steadily decrease from 92.6% to 85.3% after 8 weeks storage at 40° C./75% RH. A maximum value of 10.42% w/w of drug related impurities was also found for the same sample. This suggested vast degradation of the Clopidogrel Bisulfate in the sample. Croscarmellose Sodium was not tested any further after 8 weeks and deemed incompatible with Clopidogrel Bisulfate and Omeprazole EC Pellets.

Omeprazole EC Pellets, Clopidogrel Bisulfate and Mannitol were mixed in a ratio of 1.00:0.40:1.20. The % recovery of Clopidogrel Bisulfate after 12 weeks storage at 40° C./75% RH was found to be 93.5%. This result suggested slight degradation of Clopidogrel Bisulfate had occurred. The amount (2.77% w/w) of drug related impurities in the sample at that same time point and storage conditions also suggested slight degradation had occurred. This degradation was mostly seen at a relative retention time of 0.66 in the HPLC chromatogram which was known to be a degradant of Clopidogrel Bisulfate itself. The amount of Mannitol in the sample was three times the amount of what would be found in the capsule formulation. For this reason, Mannitol was not a concern as an incompatible excipient in the clopidogrel/omeprazole capsule formulation.

Hydroxypropylcellulose also displayed a slow and steady increase in the total amount of related impurities, a final maximum value of 3.75% w/w at 12 weeks 40° C./75% RH. The bulk of the impurities are found at the relative retention time of 0.66 in the HPLC chromatogram which again was known to be an inherent degradant of Clopidogrel Bisulfate. The % recovery of Clopidogrel Bisulfate was acceptable until 12 weeks 40° C./75% RH in which % recovery was 93.1%. This value in terms of mass balance correlated to the higher amount of degradation products found in the same sample at that same time point and storage conditions. The amount of hydroxypropylcellulose in the sample preparation was more then five times the amount that would be found in the capsule formulation and the conditions in which the sample was subjected to were considered severe (40° C./75% RH). Therefore hydroxypropylcellulose was considered in the formulation of the clopidogrel/omeprazole capsules.

The sample containing Povidone K29-32 at 6 weeks 40° C./75% RH exhibited abnormal % It recovery and % w/w of related substance, 77.6% and 12.32% w/w respectively, due to possible contamination of sample during sample preparation. Samples of the remaining time points showed no incompatibilities. For this reason, this excipient was still considered as a prospective excipient for the formulation.

A low % recovery of Clopidogrel Bisulfate was obtained when testing the initial sample of the hydroxypropylmethylcellulose mixture. This could be attributed to analytical error as the 1, 2 and 4 weeks samples exhibited acceptable % recovery of Clopidogrel Bisulfate. A noteworthy decrease in the % recovery (91.1%) of Clopidogrel Bisulfate was found after 8 weeks 40° C./75% RH. This could also be correlated with a higher % w/w of related impurities (1.37%) found compared to the initial value of 0.85% w/w. At 12 weeks 40° C./75% RH, the results of both Clopidogrel Bisulfate recovery and related substances increased and found to be satisfactory. The major contributor to the % w/w of drug related impurities was found at around 0.66 relative retention time in the HPLC chromatogram. As previously described, this impurity was possibly a degradant of Clopidogrel Bisulfate itself.

The remainder of the excipients showed no considerable decline in % recovery of Clopidogrel Bisulfate over the 12 weeks and storage at 40° C./75% RH. They all contained low % w/w of drug related impurities/degradation products. All excipients with the exception of Croscarmellose Sodium were considered compatible with Clopidogrel Bisulfate and Omeprazole EC Pellets. Thus they could be used in the clopidogrel/omeprazole capsule formulations.

Based on the results generated from this study, the following excipients are considered compatible with Clopidogrel Bisulfate and Omeprazole Enteric Coated Pellets and could be used in the clopidogrel/omeprazole capsule formulation development.

Mannitol
Microcrystalline Cellulose
Hydroxypropylcellulose
Polyethylene Glycol 6000
Hydrogenated Castor Oil
Povidone K 29-32
Lactose 316 Fast Flo (monohydrate)
Hydroxypropylmethylcellulose
White/White Opaque Capsule Example 7

Hard Gelatin Capsules—Clopidogrel Granules and Enteric Coated Omeprazole Granules This example demonstrates an embodiment of a capsule oral dosage form with clopidogrel granules and enteric coated omeprazole granules (Table 1). Enteric coated omeprazole granules containing between 7-10% omeprazole, and excipients can include but are not limited to lactose, magnesium stearate, mannitol, microcrystalline cellulose, crospovidone and disodium hydrogen diphosphate. The enteric coating is deposited on the granules between 5-20% by weight and may include but not limited to methacrylic acid copolymers, cellulose acetate phthalate, hydroxypropyl methylcellulose phthalate, polyvinyl acetate phthalate. Clopidogrel granules can include but are not limited to microcrystalline cellulose, mannitol, pregelatinized starch. PEG 6000 and hydrogenated castor oil. The enteric coated omeprazole granules are blended with the clopidogrel granules and filled into either hard gelatin capsules or HPMC capsules

TABLE 9

| Omeprazole granules | Clopidogrel granules |
| --- | --- |
| 20 mg omeprazole | 75 mg clopidogrel |
| 100 mg lactose | 10 mg pregelatinized starch |
| 30 mg microcrystalline cellulose | 50 mg microcrystalline cellulose |
| 20 mg mannitol | 25 mg mannitol |
| 25 mg disodium hydrogen phosphate | 2 mg hydrogenated castor oil |
| 3 mg crospovidone | |
| 2 mg magnesium stearate | |
| Enteric film coating at 10% weight gain containing hydroxypropyl methylcellulose phthlate plasticized by triethyl citrate | |

Example 8

Hard Gelatin Capsules—250 mg Ticlopidine and 10 mg Famotidine

This example demonstrates embodiments of capsule oral dosage forms with ticlopidine granules and famotidine granules (Table 10).

Ticlopidine HCl is granulated with microcrystalline cellulose, citric acid, magnesium stearate, croscarmellose sodium and povidone. Famotidine is granulated with microcrystalline cellulose, croscarmellose sodium, mannitol, magnesium stearate. The ticlopidine HCl granules and famotidine granules are blended and filled into hard gelatin or HPMC capsules.

Alternatively, ticlopidine HCl and famotidine are granulated into a common granule with microcrystalline cellulose citric acid, croscarmellose sodium, povidone and magnesium stearate. The granules are filled into either hard gelatin or HPMC capsules.

TABLE 10

| Ticlopidine granules | Famotidine granules |
|---|---|
| 250 mg ticlopidine base as HCl salt | 10 mg famotidine |
| 100 mg microcrystalline cellulose | 50 mg microcrystalline cellulose |
| 25 mg citric acid | 15 mg mannitol |
| 25 mg povidone | 2.5 mg croscarmellose sodium |
| 11 mg croscarmellose sodium | 0.5 mg magnesium stearate |
| 4 mg magnesium stearate | |

Example 9

Hard Gelatin Capsules—Sulfinpyrazone, 100 mg and Enteric Coated Omeprazole Granules, 20 mg This example demonstrates an embodiment of a capsule oral dosage form with sulfinpyrazone granules and enteric coated omeprazole granules (Table 11).

Enteric coated omeprazole granules are prepared as described in Example 1. Sulfinpyrazone is granulated with lactose, croscarmellose sodium, magnesium stearate and colloidal silica. She sulfinpyrazone granules are blended with the enteric coated granules and filled into either hard gelatin capsules or HPMC capsules.

TABLE 11

| Omeprazole granules | Sulfinpyrazone granules |
|---|---|
| 20 mg omeprazole | Sulfinpyrazone 100 mg |
| 100 mg lactose | Lactose 80 mg |
| 30 mg microcrystalline cellulose | Colloidal silica 2 mg |
| 20 mg mannitol | Magnesium stearate 1 mg |
| 25 mg disodium hydrogen phosphate | Croscarmellose sodium 3 mg |
| 3 mg crospovidone | |
| 2 mg magnesium stearate | |
| Enteric film coating at 10% weight gain containing hydroxypropyl methylcellulose phthlate plasticized by triethyl citrate | |

Example 10

Hard Gelatin Capsules—Sulfinpyrazone, 100 mg and Enteric Coated Lansoprazole Granules, 15 or 30 mg This example demonstrates an embodiment of a capsule oral dosage form with sulfinpyrazone granules and enteric coated lansoprazole granules (Table 12).

Sulfinpyrazone granules are prepared as described in Example 9. Lansoprazole is granulated with magnesium carbonate, starch, lactose and sucrose. The granules are enteric coated with methacrylic acid copolymers plasticized with triethyl citrate. The enteric coated lansoprazole granules are blended with the sulfinpyrazone granules and filled into either hard gelatin or HPMC capsules.

TABLE 12

| Lansoprazole granules | Sulfinpyrazone granules |
|---|---|
| 15 mg lansoprazole | Sulfinpyrazone 100 mg |
| 50 mg magnesium carbonate | Lactose 80 mg |
| 50 mg lactose | Colloidal silica 2 mg |

TABLE 12-continued

| Lansoprazole granules | Sulfinpyrazone granules |
|---|---|
| 30 mg sucrose | Magnesium stearate 1 mg |
| 15 mg pregelatinized starch | Croscarmellose sodium 3 mg |
| Enteric film coating at 10% weight gain containing methacrylic acid copolymers plasticized with triethyl citrate | |

Example 11

Hard Gelatin Capsules Clopidogrel, 75 mg and Enteric Coated Esomeprazole, 20 mg or 40 mg This example demonstrates an embodiment of a capsule oral dosage form with clopidogrel bisulfate and enteric coated esomeprazole.

Clopidogrel granules are prepared as described in Example 1 or 7. Esomeprazole is granulated with microcrystalline cellulose, crospovidone and sodium stearyl fumarate. The granules are enteric coated with methacrylic acid copolymers plasticized with triethyl citrate. The enteric coated esomeprazole granules are blended with the clopidogrel granules and filled into either hard gelatin or HPMC capsules.

TABLE 13

| Esomeprazole granules | Clopidogrel granules |
|---|---|
| 20 mg esomeprazole | 75 mg clopidogrel |
| 100 mg microcrystalline cellulose | 10 mg pregelatinized starch |
| 10 mg Crospovidone | 50 mg microcrystalline cellulose |
| 5 mg sodium stearyl fumarate | 25 mg mannitol |
| Enteric film coating at 10% weight gain containing methacrylic acid copolymers plasticized with triethyl citrate | 2 mg hydrogenated castor oil |

Example 12

Hard Gelatin Capsules—Clopidogrel, 75 mg and Ranitidine, 75 mg or 150 mg

This example demonstrates an embodiment of a capsule oral dosage form with clopidogrel and ranitidine HCl.

Rantidine HCl is granulated with microcrystalline cellulose, croscarmellose sodium and magnesium stearate. These granules are blended with the clopidogrel granules prepared according to Example 1 or 7 and filled into either hard gelatin or HPMC capsules.

Alternatively clopidogrel bisulfate and ranitidine HCl granulated into a common granule with microcrystalline cellulose, croscarmellose sodium and hydrogenated castor oil. The granules are filled into either hard gelatin or HPMC capsules.

TABLE 14

| Ranitidine granules | Clopidogrel granules |
|---|---|
| 75 mg ranitidine base as HCl salt | 75 mg clopidogrel |
| 75 mg microcrystalline cellulose | 10 mg pregelatinized starch |
| 5 mg croscarmellose sodium | 50 mg microcrystalline cellulose |
| 1 mg magnesium stearate | 25 mg mannitol |
| | 2 mg hydrogenated castor oil |

Example 13

Enteric Coated Capsule Formulations

Formulations described in Examples 7, 9, 10 and 11 can be prepared without enteric coating the acid labile proton pump inhibitor and the capsules are enteric coated to a 15% weight gain. Granules of the two different actives are filled into either hard gelatin capsules or HPMC capsules. The capsules are enteric coated using either methacrylic acid copolymers or polyvinyl acetate phthalate or other enteric polymers. The film coatings may contain colorants and other common additives.

Example 14

Non-Enteric Coated Tablet Formulations

The formulations described in Examples 8 and 12 can be prepared as tablets. Following granulation of the active ingredients as described in the examples, the granules of the individual actives are blended, sized and lubricated with 0.5% by weight magnesium stearate and compressed into conventional gastric disintegrating tablets. The tablets are film coated at a 5% weight gain with hydroxypropyl methyl cellulose, plasticized with triacetin and also containing titanium dioxide and/or talc as opacifying agents and colorants. The film can provide taste masking if required.

Example 15

Enteric Coated Tablet Formulations

The formulations described in Examples 7, 9, 10 and 11, containing an acid labile proton pump inhibitor can be prepared as enterically coated tablets. The granules of the individual actives are prepared as described in the examples without enteric coating the proton pump inhibitor granules. Granules of the two actives are blended, sized and lubricated, and compressed into a tablet and the tablets are enteric coated using either methacrylic acid copolymers or polyvinyl acetate phthalate or other enteric polymers to a 10-15% weight gain. The film coatings may contain colorants, opacifiers and other common additives.

Example 16

Chewable Tablets

This example demonstrates embodiments of chewable tablet oral dosage forms with clopidogrel bisulfate and famotidine (Table 15).

Clopidogrel (75 mg) and famotidine (10 mg) are granulated with mannitol, maltodextrin, aspartame, citric acid, microcrystalline cellulose, magnesium stearate and flavoring and color agents. The granules are compressed into a chewable tablet.

To further enhance the acid inhibitory effect of the formulation, pH control agents can be added to the granulations. Clopidogrel (75 mg), famotidine (10 mg), calcium carbonate (500 mg) and magnesium hydroxide (100 mg) are granulated with mannitol and/or lactose, magnesium stearate, flavors, sugar and colorants and compressed into chewable tablets.

TABLE 15

| |
|---|
| 75 mg clopidogrel |
| 10 mg famotidine |
| 80 mg microcrystalline cellulose |
| 240 mg mannitol |
| 25 mg maltodextrin |
| 5 mg aspartame |
| 25 mg citric acid |
| 5 mg magnesium stearate |
| Cherry or citrus flavor and red ferric oxide |

Example 17

(a) Excipients for Tablet in Clopidogrel Component 97.875 mg clopidogrel bisulphate, microcrystalline cellulose, mannitol, hydroxypropylcellulose, polyethylene glycol 6000, 1% hydrogenated castor oil, film coated or not (b) Excipients for Omeprazole Component polyvinylpyrrolindone, hypromellose, polyethylene glycol 6000, polysorbate 80, glyceryl monostearate, on sucrose, then methacrylic acid, triethylcitrate, sodium stearyl fumarate and tablet from blend in microcrystalline cellulose, starch, hydroxypropylcellulose, talc, magnesium stearate The clopidogrel and omeprazole are combined into a tablet with one or more of the above excipients mixed in separate portions of the tablet with the clopidogrel and/or omeprazole, so long as a barrier such as an enteric coat separates the two active ingredients.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A single unit oral dosage form comprising: a) an adenosine diphosphate (ADP) or $P_2Y_{12}$ antagonist or a pharmaceutically acceptable salt or enantiomer thereof, in a therapeutically effective amount to provide antiplatelet activity; and b) a proton pump inhibitor (PPI) or a pharmaceutically acceptable salt or enantiomer thereof, in a therapeutically effective amount to prevent or reduce a gastrointestinal disorder associated with use of said ADP or $P_2Y_{12}$ antagonist or said ADP or $P_2Y_{12}$ antagonist and aspirin, wherein said PPI, is enterically coated.

2. The single unit oral dosage form of claim 1, wherein said ADP or $P_2Y_{12}$ antagonist or pharmaceutically acceptable salt or enantiomer thereof is clopidogrel and said PPI or pharmaceutically acceptable salt or enantiomer thereof is omeprazole.

3. The single unit oral dosage form of claim 2, wherein the clopidogrel or pharmaceutically acceptable salt or enantiomer thereof is a powder and the omeprazole or pharmaceutically acceptable salt or enantiomer thereof is enterically coated.

4. The single unit oral dosage form of claim 3, wherein the clopidogrel or pharmaceutically acceptable salt or enantiomer thereof and omeprazole or pharmaceutically acceptable salt or enantiomer thereof are disposed within a capsule.

5. The single unit oral dosage form of claim 2, wherein the clopidogrel or pharmaceutically acceptable salt or enantiomer thereof is present in an amount of 20-200 mg and the omeprazole or pharmaceutically acceptable salt or enantiomer thereof is present in an amount of about 10-100 mg.

6. The single unit oral dosage form of claim 2, wherein the clopidogrel or pharmaceutically acceptable salt or enantiomer thereof is present in an amount of 20-200 mg and the omeprazole or pharmaceutically acceptable salt or enantiomer thereof is present in an amount of about 10-100 mg.

7. The single unit oral dosage form of claim 4, wherein the clopidogrel or pharmaceutically acceptable salt or enantiomer thereof is present in an amount of 20-200 mg and the omeprazole or pharmaceutically acceptable salt or enantiomer thereof is present in an amount of about 10-100 mg.

8. The single unit oral dosage form of claim 5, wherein the clopidogrel or pharmaceutically acceptable salt or enantiomer thereof is present in an amount of 75 mg and the omeprazole or pharmaceutically acceptable salt or enantiomer thereof is present in an amount of 20 mg.

9. The single unit oral dosage form of claim 6, wherein the clopidogrel or pharmaceutically acceptable salt or enantiomer thereof is present in an amount of 75 mg and the omeprazole or pharmaceutically acceptable salt or enantiomer thereof is present in an amount of 20 mg.

10. The single unit oral dosage form of claim 7, wherein the clopidogrel or pharmaceutically acceptable salt or enantiomer thereof is present in an amount of 75 mg and the omeprazole or pharmaceutically acceptable salt or enantiomer thereof is present in an amount of 20 mg.

11. A combination of the single unit oral dosage form of any one of claims 1, 2, 3, 4, or 5-10, together with an oral dosage form comprising aspirin.

12. The single unit oral dosage form of any one of claims 1, 2, 3, 4, or 5-10, further comprising aspirin.

13. The single unit oral dosage form of any one of claims 1, 2, 3, 4, or 5-10, wherein said single unit oral dosage form excludes a non-aspirin non-steroidal anti-inflammatory drug (NSAID).

14. A method of treating a patient who is in need of antiplatelet therapy and does not have symptoms of gastrointestinal bleeding or a gastrointestinal ulcer, comprising orally administering to said patient the single unit oral dosage form of any one of claims 5-10.

15. A method of treating a patient who is in need of antiplatelet therapy and does not have symptoms of gastrointestinal bleeding or a gastrointestinal ulcer, comprising orally administering to said patient the combination of oral dosage forms recited in claim 11.

16. A method of treating a patient who is in need of antiplatelet therapy and does not have symptoms of gastrointestinal bleeding or a gastrointestinal ulcer, comprising orally administering to said patient the single unit oral dosage form recited in claim 12.

* * * * *